US008722724B2

(12) United States Patent
Anderson et al.

(10) Patent No.: US 8,722,724 B2
(45) Date of Patent: May 13, 2014

(54) COMPOSITIONS AND METHODS FOR TREATING NEOPLASTIC DISEASES

(75) Inventors: Kenneth C. Anderson, Wellesley, MA (US); Dharminder Chauhan, Natick, MA (US); Michael A. Palladino, Olivenhain, CA (US)

(73) Assignees: Triphase Research and Development I Corp. (CA); Dana-Farber Cancer Institute, Inc., Boston, MA (US)

( * ) Notice: Subject to any disclaimer, the term of this patent is extended or adjusted under 35 U.S.C. 154(b) by 852 days.

(21) Appl. No.: 12/183,007

(22) Filed: Jul. 30, 2008

(65) Prior Publication Data

US 2009/0036390 A1 Feb. 5, 2009

Related U.S. Application Data

(63) Continuation of application No. 11/293,354, filed on Dec. 2, 2005, now abandoned.

(60) Provisional application No. 60/633,161, filed on Dec. 3, 2004.

(51) Int. Cl.
*A61K 31/407* (2006.01)

(52) U.S. Cl.
CPC .................................. *A61K 31/407* (2013.01)
USPC ......................................................... 514/421

(58) Field of Classification Search
CPC ................................................... A61K 31/407
See application file for complete search history.

(56) References Cited

U.S. PATENT DOCUMENTS

| | | | |
|---|---|---|---|
| 5,445,829 A | 8/1995 | Paradissis et al. | |
| 5,576,012 A | 11/1996 | Bauer et al. | |
| 5,601,845 A | 2/1997 | Buxton et al. | |
| 5,641,515 A | 6/1997 | Ramtoola | |
| 5,653,987 A | 8/1997 | Modi et al. | |
| 5,654,286 A | 8/1997 | Hostetler | |
| 5,667,809 A | 9/1997 | Trevino et al. | |
| 5,683,676 A | 11/1997 | Akehurst et al. | |
| 5,688,529 A | 11/1997 | Lidgate et al. | |
| 5,707,615 A | 1/1998 | Cardin et al. | |
| 5,707,641 A | 1/1998 | Gertner et al. | |
| 5,726,181 A | 3/1998 | Hausheer et al. | |
| 5,733,888 A | 3/1998 | Carver et al. | |
| 5,756,764 A | 5/1998 | Fenteany et al. | |
| 5,874,443 A | 2/1999 | Kiely et al. | |
| 5,886,210 A | 3/1999 | Rayle et al. | |
| 5,922,683 A | 7/1999 | Or et al. | |
| 6,133,308 A | 10/2000 | Soucy et al. | |
| 6,147,223 A | 11/2000 | Fenteany et al. | |
| 6,214,862 B1 | 4/2001 | Fenteany et al. | |
| 6,271,199 B2 | 8/2001 | Brand et al. | |
| 6,294,560 B1 | 9/2001 | Soucy et al. | |
| 6,333,358 B1 | 12/2001 | Nakazato et al. | |
| 6,335,358 B1 | 1/2002 | Fenteany et al. | |
| 6,350,759 B1 | 2/2002 | Casara et al. | |
| 6,458,825 B1 | 10/2002 | Fenteany et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,566,553 B2 | 5/2003 | Soucy et al. | |
| 6,645,999 B1 | 11/2003 | Schreiber et al. | |
| 6,794,516 B2 | 9/2004 | Soucy et al. | |
| 6,838,477 B2 | 1/2005 | Schreiber et al. | |
| 6,849,743 B2 | 2/2005 | Soucy et al. | |
| 7,144,723 B2 | 12/2006 | Fenical et al. | |
| 7,176,232 B2 | 2/2007 | Fenical et al. | |
| 7,176,233 B2 | 2/2007 | Fenical et al. | |
| 7,179,834 B2 | 2/2007 | Fenical et al. | |
| 7,183,417 B2 | 2/2007 | Corey | |
| 7,276,530 B2* | 10/2007 | Potts et al. ................... 514/421 |
| 7,371,875 B2 | 5/2008 | Xiao et al. | |
| 7,511,156 B2 | 3/2009 | Corey | |
| 7,544,814 B2 | 6/2009 | Potts et al. | |
| 7,572,606 B1 | 8/2009 | Lam et al. | |
| 7,579,371 B2 | 8/2009 | Palladino et al. | |
| 7,635,712 B2 | 12/2009 | Fenical et al. | |
| 7,879,576 B2 | 2/2011 | Fenical et al. | |
| 7,910,616 B2 | 3/2011 | Macherla et al. | |
| 7,928,138 B2 | 4/2011 | Fenical et al. | |
| 2001/0002391 A1 | 5/2001 | Brand et al. | |
| 2001/0051654 A1 | 12/2001 | Elliott et al. | |
| 2003/0157695 A1 | 8/2003 | Fenical et al. | |
| 2004/0138196 A1* | 7/2004 | Fenical et al. ............... 514/192 |
| 2005/0049294 A1 | 3/2005 | Palladino et al. | |
| 2005/0203029 A1 | 9/2005 | Schubert et al. | |

(Continued)

FOREIGN PATENT DOCUMENTS

CA  2429163  6/2002
WO  WO 96/32105  10/1996

(Continued)

OTHER PUBLICATIONS

Feling et al. Angew. Chem. Int. Ed., 2003, vol. 42, No. 3, pp. 355-357.*
Fenical et al. Bioorganic & Medicinal Chemistry, 2009, vol. 17, pp. 2175-2180.*
Chauhan et al. Blood, Nov. 16, 2004, vol. 104, No. 11, Part 1, p. 661A (Abstract attached).*
Richardson, Expert Opin. Pharmacother., 2004, vol. 5, No. 6, pp. 1321-1331.*
Adams, et al., "Proteasome Inhibitors: A Novel Class of Potent and Effective Antitumor Agents," *Cancer Res.*, (1999) 59:2615-2622.
Adams, J., "The Development of Novel Targeted Therapeutics for Treatment of Multiple Myeloma Research Roundtable," *Euro. J. Haematology*, (2003) 70:265.
Adams, J., "Proteasome Inhibitors as New Anticancer Drugs," *Curr. Opin. Oncol.*, (2002) 14:628-34.
Alessandri, et al., "Mobilization of Capillary Endothelium In Vitro Induced by Effectors of Angiogenesis In Vivo," *Cancer Res.*, (1983) 43(4):1790-1797.
Alm, et al., "Effects of Topically Applied PGF2 and its Isopropylester on Normal and Glaucomatous Human Eyes," *Prog. Clin. Biol. Res.*, (1989) 312:447-58.

(Continued)

*Primary Examiner* — James D Anderson
(74) *Attorney, Agent, or Firm* — Cooley LLP

(57) ABSTRACT

Disclosed herein are compositions and methods for treating neoplastic diseases. Included are compositions and methods that are effective against multiple myeloma cells resistant to conventional and bortezomib treatment. Furthermore, combination treatment with two different proteosome inhibitors is shown to be synergistic for treating multiple myeloma.

9 Claims, 21 Drawing Sheets

(56) References Cited

U.S. PATENT DOCUMENTS

| | | |
|---|---|---|
| 2005/0203162 A1 | 9/2005 | Xiao et al. |
| 2005/0239866 A1 | 10/2005 | Fenical et al. |
| 2006/0008852 A1 | 1/2006 | Fenical et al. |
| 2006/0229353 A1 | 10/2006 | Stadler et al. |
| 2006/0264495 A1 | 11/2006 | Palladino et al. |
| 2006/0287520 A1 | 12/2006 | Danishefsky et al. |
| 2007/0004676 A1 | 1/2007 | Palladino et al. |
| 2007/0155815 A1 | 7/2007 | Fenical et al. |
| 2007/0161693 A1 | 7/2007 | Corey |
| 2007/0225350 A1 | 9/2007 | Anderson et al. |
| 2008/0070273 A1 | 3/2008 | Fenical et al. |
| 2008/0070969 A1 | 3/2008 | Potts et al. |
| 2008/0280968 A1 | 11/2008 | Palladino et al. |
| 2009/0036390 A1 | 2/2009 | Anderson et al. |
| 2009/0062547 A1 | 3/2009 | Romo et al. |
| 2009/0069401 A1 | 3/2009 | Fenical et al. |
| 2009/0148445 A1 | 6/2009 | Bonavida et al. |
| 2009/0156469 A1 | 6/2009 | Ghobrial et al. |
| 2009/0197937 A1 | 8/2009 | Fenical et al. |
| 2009/0298906 A1 | 12/2009 | Macherla et al. |
| 2009/0318529 A1 | 12/2009 | Fenical et al. |
| 2010/0144826 A1 | 6/2010 | Fenical et al. |
| 2010/0168046 A1 | 7/2010 | Palladino et al. |

FOREIGN PATENT DOCUMENTS

| | | |
|---|---|---|
| WO | WO 98/35691 | 8/1998 |
| WO | WO 99/09006 | 2/1999 |
| WO | WO 99/15183 | 4/1999 |
| WO | WO 00/23614 | 4/2000 |
| WO | WO 02/47610 | 6/2002 |
| WO | WO 2004/043374 | 5/2004 |
| WO | WO 2004/071382 | 8/2004 |
| WO | WO 2005/002572 | 1/2005 |
| WO | WO 2005/003137 | 1/2005 |
| WO | WO 2006/028525 | 3/2005 |
| WO | WO 2005/094423 | 10/2005 |
| WO | WO 2005/099687 | 10/2005 |
| WO | WO 2006/005551 | 1/2006 |
| WO | WO 2006/060609 | 6/2006 |
| WO | WO 2006/060676 | 6/2006 |
| WO | WO 2006/060809 | 6/2006 |
| WO | WO 2006/118973 | 11/2006 |
| WO | WO 2007/021897 | 2/2007 |
| WO | WO 2007/033039 | 3/2007 |
| WO | WO 2007/130404 | 11/2007 |
| WO | WO 2007/138116 | 12/2007 |
| WO | WO 2008/137780 | 11/2008 |

OTHER PUBLICATIONS

Beers, et al., (Eds.), "Bacterial Diseases," *The Merck Manual of Diagnosis and Therapy*, (1999) The Merck Research Laboratories, Whitehouse Station N.J., Section 13, Chapter 157: pp. 1157-1158.
Beers, et al., (Eds.), "Parasitic Infections," *The Merck Manual of Diagnosis and Therapy*, (1999) The Merck Research Laboratories, Whitehouse Station N.J., Section 13, Chapter 161: pp. 1241-1252.
Beers, et al., (Eds.), *The Merck Manual of Diagnosis and Therapy*, 17th Ed. 1999, The Merck Research Laboratories, Whitehouse Station N.J., pp. 397-399, 948-949, 1916-1917, 1974-1975 and 1978-1983.
Beers, et al., (Eds.), *The Merck Manual of Diagnosis and Therapy*, 17th Ed. 1999, The Merck Research Laboratories, Whitehouse Station N.J., pp. 1193-1201 & 1204.
Beers, et al., (Eds), "The Merck Manual of Diagnosis and Therapy", 17th Ed. 1999, The Merck Research Laboratories, Whitehouse Station N.J., pp. 1085-1088, 1101-1135, and 1237-1276.
Bernan, et al., "Marine Microorganisms as a Source of New Natural Products," *Advances in Applied Microbiology*, (1997) 43:57-90.
Bhalla, et al., "High-Dose Mitoxantrone Induces Programmed Cell Death or Apoptosis in Human Myeloid Leukemia Cells," *Blood*, (1993) 82(10):3133-3140.
Bicknell, et al., (Eds.), *Tumour Angiogenesis*, Oxford University Press, New York (1997), Table of Contents, pp. 5.

Blum, et al., "Adriamycin: A New Anticancer Drug with Significant Clinical Activity," *Ann Intern Med*, (1974) 80(2):249-259.
Blunt, et al., "Marine Natural Products," *Nat. Prod. Rep.*, (2003) 20:1-48.
Bodart, et al., "Anthrax, MEK and Cancer," *Cell Cycle*, (2002) 1:10-15.
Bradley, et al., "Identification of the Cellular Receptor for Anthrax Toxin," *Nature*, (2001) 414:225-229.
Brosius, et al., "Complete nucleotide sequence of a 16S ribosomal RNA gene from *Eschericia coli*," *Biochemistry*, (1978) 75(10)4801-4805.
Bull, et al., "Search and Discovery Strategies for Biotechnology: the Paradigm Shift," *Microbiol. Mol. Biol. Rev.*, (2000) 64(3):573-606.
Carey, Francis, *Organic Chemistry*, 2nd ed., McGraw Hill, Inc., New York (1992), pp. 328-331.
Chauhan, et al., "A Novel Orally Active Proteasome Inhibitor Induces Apoptosis in Multiple Myeloma Cells with Mechanisms Distinct from Bortezomib," *Cancer Cell*, (2005) 8:407-419.
Chauhan, et al., "A Novel Proteasome Inhibitor NPI-0052 as an Anticancer Therapy," *British Journal of Cancer*, (2006) 95(8):961-965.
Cheng, et al., "Arenaric Acid, a New Pentacyclic Polyether Produced by a Marine Bacterium (Actinomycetales)", *J. Nat. Prod.*, (1999) 62:605-607.
Cheng, et al., "Luisols A and B, New Aromatic Tetraols Produced by an Estuarine Marine Bacterium of the Genus *Streptomyces* (Actinomycetales)," *J. Nat. Prod.*, (1999) 62:608-610.
Ciechanover, et al., (Eds.) "The Ubiquitin-Proteasome Proteolytic System—From Classical Biochemistry to Human Diseases" by Baumeister et al., (2002) pp. 68-70.
Claverol, et al., "Mapping and Structural Dissection of Human 20 S Proteasome Using Proteomic Approaches," *Mol Cell Proteomics*, (2002) 1:567-78.
Cole, et al., "The Ribosomal Database Project (RDP-II): sequences and tools for high-throughput rRNA analysis," *Nucleic Acids Research*, (2005) 33: D294-D296.
Colquhoun, et al, "Rapid Characterization of Deep-Sea Actionmycetes for Biotechnology Screening Programmes", *Antonie Van Leeuwenoek*, (2000) 77:359-367.
Colquhoun, et al., "Novel Rhodococci and Other Mycolate Actinomycetes From the Deep Sea," *Antonie van Leeuwenhoek*, (1998) 74:27-40.
Colquhoun, et al., "Taxonomy and Biotransformation Activites of Some Deep-Sea Actinomycetes," *Extremophiles*, (1998) 2:269-277.
Corey et al., "The Structural Requirements for Inhibition of Proteasome Function by the Lactacystin-derived beta-lactone and Synthetic Analogs," *Tetrahedron* (1999) 55(11):3305-3316.
Corey, et al., "Total Synthesis of Lactacystin," *J. Am. Chem. Soc.*, (1992) 114(26):10677-10678.
Corey, et al., "An Efficient Total Synthesis of a New and Highly Active Analog of Lactacystin," *Tetrahedron Letters*, (1998) 39:7475-7478.
Cragg, et al., "Chemical Diversity: A Function of Biodiversity," *Trends Pharmacol. Sci.*, (2002) 23:404-5.
Crane, et al., "A Novel Enantioselective Synthetic Route to Omuralide Analogues with the Potential for Species Selectivity in Proteasome Inhibition," *Organic Letters*, (2001) 1395-1397.
Crueger, et al., (Eds.), *Biotechnology: A Textbook of Industrial Microbiology*, 2nd ed. (English Edition, Thomas D. Brock Ed.), Sinauer Associates Inc, Sunderland MA, (1990) Chapter 2:4-8.
Cusack, et al., "Enhanced Chemosensitivity to CPT-11 with Proteasome Inhibitor PS-341: Implications for Systemic Nuclear Factor-kB Inhibition", *Cancer Res.*, (May 1, 2001) 61(9):3535-40.
Cusack, et al., "NPI-0052 Enhances Tumoricidal Response to Conventional Cancer Therapy in a Colon Cancer Model," *Clin. Cancer Res.*, (2006) 22:6758-6764.
Cusack, et al., "Rationale for the Treatment of Solid Tumors with the Proteasome Inhibitor Bortezomib," *Cancer Treat Rev.*, (2003) 29(suppl 1): 21-31.
Davidson, Bradley S., "New Dimensions in Natural Products Research: Cultured Marine Microorganisms," *Current Opinion in Biotechnology*, (1995) 6:284-291.

(56) References Cited

OTHER PUBLICATIONS

Decker, et al., "Inhibition of Caspase-3-mediated Poly (ADP-ribose) Polymerase (PARP) Apoptotic Cleavage by Human PARP Autoantibodies and Effect on Cells Undergoing Apoptosis," *J. Biol. Chem.*, (2000) 275(12):9043-9046.
Delong, et al., "Environmental Diversity of Bacteria and Archaea," *Syst. Biol.*, (2001) 50(4):470-478.
Developmental Therapeutics Program—NCI/NIH, "DTP Human Tumor Cell Line Screen." Screening Services. DPI. Sep. 28, 2005 http://dtp.nci.nih.gov/branches/btb/ivclsp.html.
Developmental Therapeutics Program—NCI/NIH, "Cell Lines in the in Vitro Screen", online: http://dtp.nci.nih.gov/docs/misc/common_files/cell_list/html, accessed Oct. 27, 2009.
Dick, et al., "Mechanistic Studies on the Inactivation of the Proteasome by Lactacystin," *J. Biol. Chem.*, (1996) 271(13):7273-7276.
Ding, et al., "Proteasome Inhibition Induces Reversible Impairments in Protein Synthesis," *The FASEB Journal*., (2006) 20:1055-1063.
Duesbery, et al., "Proteolytic Inactivation of MAP-Kinase-Kinase by Anthrax Lethal Factor," *Science*, (1998) 280:734-737.
Elliott, et al., "The Proteasome: A New Target for Novel Drug Therapies," *American Journal of Clinical Pathology*, (Nov. 2001) 637-646.
Elliott, et al., "Proteasome Inhibition: A New Anti-Inflammatory Strategy," *J. Mol. Med.*, (2003) 81:235-245.
Endo, et al., "Total Synthesis of Salinosporamide A," *J. Am. Chem. Soc.*, (2005) 127(23): 8298-8299 and Supporting Information S1-S23.
Erba, et al., "Mode of Action of Thiocoraline: A Natural Marine Compound With Anti-Tumor Activity," *British Journal of Cancer*, (1999) 88(7):971-980.
Escuyer, et al., "Anthrax Protective Antigen Interacts with a Specific Receptor on the Surface of CHO-K1 Cells," *Infect. Immun.*, (1991) 59(10):3381-3386.
Faulkner, D. John, "Marine Natural Products," *Nat. Prod. Rep.*, (2001) 18(1):1-49.
Fenical, et al., "Marine Microorganisms as a Biomedical Source: Are They Unculturable or Uncultured?" PowerPoint Presentation, Center for Marine Biotechnology and Biomedicine (Feb. 24, 2002).
Fenical, et al., "Marine Microorganisms as a Developing Resource for Drug Discovery," *Pharmaceutical News*, (2002) 9:489-494.
Fenical, et al., "Salinospora, a Major New Marine Actinomycete Taxon for Drug Discovery, Powerpoint Presentation, Center for Marine Biotechnology and Biomedicine" (Jun. 24, 2001).
Fenical, William, "Chemical Studies of Marine Bacteria: Developing a New Resource," *Chem. Rev.*, (1993) 93(5):1673-1683.
Fenical, William, "New Pharmaceuticals From Marine Organisms," *Marine Biotechnology*, (1997) 15:339-341.
Fenteany, et al., "Lactacystin, Proteasome Function, and Cell Fate," *J. Biol. Chem*. (1998) 273(15): 8545-8548.
Fenteany, et al., "Inhibition of Proteasome Activities and Subunit-Specific Amino-Terminal Threonine modification by Lactacystin," *Science*, (1995) 268:726-731.
Fernandez-Chimeno, et al., "IB-96212, a Novel Cytotoxic Macrolide Produced by a Marine *Micromonospora*," *Journal of Antibiotics*, (2000) 53(5):474-478.
Fingl, et al., "General Principals," *The Pharmaceutical Basis of Therapeutics*, 5th Ed., (Goodman et al. Eds., 1975), MacMillan Publishing Co. Inc., New York, Chapter 1:1-46.
Folkman, Judah, "Angiogenesis-Dependent Diseases," *Seminars in Oncology*, (Dec. 2001) 28:536-542.
Folkman, Judah, "Tumor Angiogenesis," *Adv Cancer Res*., (1985) 43:175-203.
Fukuchi, et al., "Direct proteasome inhibition by *clasto*-lactacystin β-lactone permits the detection of ubiquitinated p21 in ML-1 Cells," *Biochem. Biophys. Acta*, (1999) 1451:206-210.
Gale, et al., (Eds.), *The Molecular Basis of Antibiotic Action*, 2nd ed., John Wiley and Sons, London (1981) Table of Contents, pp. 1-13.
Gantt, et al., "Proteasome Inhibitors Block Development of Plasmodium SPP", *Antimicrobial Agents and Chemotherapy*, (1998) 2731-2738.

Geier, et al., "A Giant Protease with Potential to Substitute for Some Functions of the Proteasome," *Science*, (1999) 283:978-981.
Gennaro, A.R. (Ed.), *Remington'S Pharmaceutical Sciences*, 17th Ed., Mack Publishing Co., Easton, PA, (1985), Table of Contents, pp. 5.
Gennaro, A.R. (Ed.), *Remington'S Pharmaceutical Sciences*, 18th Ed., Mack Publishing Co., Easton, PA (1990), Table of Contents, pp. 5.
Giannangeli et al., "Effect of Modifications of the Alkylpiperazine Moiety of Trazodone on $5HT_{2A}$ and $_{a1}$ Receptor Binding Affinity," *J. Med. Chem.*, (1999) 42(3):336-45.
Giovannoni, Stephen, "Oceans of Bacteria," *Nature*, (Jul. 29, 2004) 430:515-16.
Goldberg, et al., "Not Just Research Tools—Proteasome Inhibitors Offer Therapeutic Promise," *Natural Medicine*, (2002) 338-40.
Golub, et al., "Molecular Classification of Cancer; Class Discovery and Class Prediction by Gene Expression Monitoring", *Science*, (1999) 286:531-37.
Goodfellow, et al., "Actinomycetes in Biotechnology," *Search and Discovery of New Antibiotics*, Okami, et al., eds., Academic Press, San Diego, (1988) Chapter 2:33-67.
Goodfellow, et al., "Actinomycetes in Marine Sediments," *Biological Biochemical and Biomedical Aspects of Actinomycetes*, Ortiz-Ortiz, et al., eds., Academic Press, Inc., Orlando (1984) 453-72.
Goodfellow, et al., "Ecology of Actinomycestes," *Ann. Rev. Microbiol.*, (1983) 37:189-216.
Goodfellow, et al., "Search and Discovery of Industrially Significant Actinomycetes," *Microbial Products: New Approaches, Society for General Microbiology Symposium*, (1989) 44:343-83.
Grant, et al., "Intracellular Mechanisms Involved in Basement Membrane Induced Blood Vessel Differentiation In Vitro," *In Vitro Cell Dev. Biol.*, (1991) 27A:327-36.
Grosios, et al., "Angiogenesis Inhibition by the Novel VEGF Receptor Tyrosine Kinase Inhibitor; PTK787/ZK222584, Causes Significant Anti-Arthritic Effects in Models of Rheumatoid Arthritis," *Inflamm Res*, (2004) 53: 133-142.
Hanna, et al., "On the Role of Macrophages in Anthrax," *Proc. Natl. Acad. Sci. USA*, (1993) 90:10198-10201.
Hardt, et al., "Neomarinone, and New Cytotoxic Marinone Derivatives, Produced by a Marine Filamentous Bacterium (Actinomycetales )," *Tetrahedron Letters*, (2000) 41(13):2073-2076.
Harker, et al., "Multidrug Resistance in Mitoxantrone-Selected HL-60 Leukemia Cells in the Absence of P-Glycoprotein Overexpression", *Cancer Res.*, (1989) 49(16): 4542-4549.
He et al., "Lomaiviticins A and B, Potent Antitumor Antibiotics from *Micromonospora lomaivitiensis*," *J. Am. Chem. Soc.*, (2001) 123(22):5362-5363.
Helmke, et al., "*Rhodococcus Marinonascens* sp. nov.: An Actinomycete From the Sea," *International J. of Systematic Bacteriology*, (Apr. 1984) 34(2):127-138.
Hideshima, et al., "NF-kB as a Therapeutic Target in Multiple Myeloma," *J. Biol. Chem.*, (2002) 277(19):16639-16647.
Higuchi, et al., "Pro-Drugs as Novel Delivery Systems," vol. 14, A.C.S. Symposium Series *American Chemical Society*, Atlantic City, NJ., Sep. 10, 1974, (1975) Table of Contents, pp. 3.
Hogan, et al., "Proteasome Inhibition by a Totally Synthetic β-Lactam Related to Salinosporamide A and Omuralide," *J. Am. Chem. Soc.*, (2005) 127(44):15386-15387.
Hopwood, et al., "Genetic Manipulation of *Streptomyces* Polyketide Synthase Genes for Novel Secondary Metabolite Production," *FEMS Microbiology Reviews*, (1995) 16:233-234.
Horan, Ann C., "Aerobic Actinomycetes: A Continuing Source of Novel Natural Products," *The Discovery of Natural Products with Therapeutic Potential (Biotechnology)*, Vincent P. Gullo (Ed.), Butterworth-Heinemann, Boston (1994) Chapter 1: 1-30.
Hull, et al., "Antiangiogenic Agents Are Effective Inhibitors of Endometriosis," *J. Clinical Endocrinology Metabolism*, (2003) 88:2889-2899.
Jensen, et al., "Distribution of Actinomycetes in Near-Shore Tropical Marine Sediments," *Applied and Environmental Microbiology*, (Apr. 1991) 57(4):1102-1108.

(56) References Cited

OTHER PUBLICATIONS

Jensen, et al., "Strategies for the Discovery of Secondary Metabolites from Marine Bacteria: Ecological Perspectives," *Annu. Rev. Microbiology*, (1994) 48:559-584.

Jensen, et al., "The Relative Abundance and Seawater Requirements of Gram-Positive Bacteria in Near-Shore Tropical Marine Samples," *Microbial Ecology*, (1995) 29(3):249-257.

Jensen, et al., "Marine Microorganisms and Drug Discovery: Current Status and Future Potential," *Drugs from the Sea*, Nobuhiro Fusetani Ed., Krager, Basel Switzerland (2000) 6-29.

Jiang, et al., "Antinoflavoside, A Novel Flavonoid-Like Glycoside Produced by a Marine Bacterium of the Genus *Streptomyces*," *Tetrahedron Letters*, (1997) 38(29):5065-5068.

Johnson et al., "Relationships between drug activity in NCI preclinical in vitro and in vivo models and early clinical trials", *British J Cancer*, (2001) 84(11): 1424-1431.

Joseph, et al., "Laboratory Cultivation of Widespread and Previously Uncultured Soil Bacteria," *Applied and Environmental Microbiology*, (2003) 69(12):7210-7215.

Josh, A., "Microparticulates for Ophthalmic Drug Delivery," *J. Ocul. Pharmacol.*, (1994) 10:29-45.

Kalns, et al., "Delayed Treatment With Doxycycline Has Limited Effect on Anthrax Infection in BLK57/B6 Mice," *Biochem. Biophys. Res. Commun.*, (2002) 297:506-509.

Kalns, et al., "TNF Receptor 1, IL-1 Receptor, and iNOS Genetic Knockout Mice Are Not Protected from Anthrax Infection," *Biochem. Biophys. Res. Commun.*, (2002) 292:41-44.

Kerr, et al., "Marine Natural Products as Therapeutic Agents", Exp. Opinion on Therapeutic Patents, (1999) 9(9):1207-1222.

Kim, et al., "Sensitizing Anthrax Lethal Toxin-Resistant Macrophages to Lethal Toxin-Induced Killing by Tumor Necrosis Factor," *J. Biol. Chem.*, (2003) 278:7413-7421.

King, et al., "How Proteolysis Drives the Cell Cycle," *Science*, (1996) 274:1652-1659.

Kisselev, et al., "Proteasome Inhibitors: From Research Tools to Drug Candidates," *Chem. Biol.*, (2001) 8:739-758.

Kisselev et al., "Importance of the Different Proteolytic Sites of the Proteasome and the Efficacy of Inhibitors Varies with the Protein Substrate," J Bio Chem., (Mar. 2006) 281(13): 8582-8590.

Koch, et al., "16S Ribosomal DNA Analysis of the Genera *Micromonospora*, *Actinoplanes*, *Catellatospora*, *Catenuloplanes*, *Dactylosporangium*, and *Pillimelia* and Emendation or the Family *Micromonosporaceae*," *Intl Journal of Systematic Bacteriology*, (Jul. 1996) 46(3):765-768.

Kozlowski, et al., "Lactacystin Inhibits Cathepsin A Activity in Melanoma Cell Lines," *Tumor Biol.*, (2001) 22:211-215.

Lacy, et al., "Mapping the Anthrax Protective Antigen Binding Site on the Lethal and Edema Factors," *J. Biol. Chem.*, (2002) 277:3006-3010.

Lam, et al., "Isolation of a Bromo Analog of Rebeccamycin From *Saccharothrix aerocolonigenes*," *J. Antibiotics*, (Sep. 1991) 44(9):934-939.

Lam, et al., "Production, Isolation and Structure Determination of Novel Fluoroindolocarbazoles from *Saccharothrix aerocolonigenes* ATCC 39243," *J. Antibiotics*, (2001) 54(1):1-9.

Lawley, et al., "Induction of Morphologic Differentiation of Endothelial Cells in Culture," *J. Investigative Dermatology*, (Aug. 1989) 93(2 Supplement):59S-61S.

Lenz, et al., "Clinical Update: Proteasome Inhibitors in Solid Tumors", *Cancer Treatment Reviews*, (2003) 29 (1 Supplement):41-48.

Lightcap, et al., "Proteasome Inhibition Measurements Clinical Application," *Clin. Chem.*, (2000) 46(5):673-683.

Lin, et al., "Cytotoxic Effects of Anthrax Lethal Toxin on Macrophage-Like Cell Line J774A.1," *Curr. Microbiol.*, (1996) 33:224-227.

Liu, et al., "Angiogenesis Inhibitors May Regulate Adiposity," *Nutr. Rev.*, (2003) 61:384-387.

Liu, et al., "Precursor Supply for Polyketide Biosynthesis: The Role of Crotonyl-CoA Reductase," *Metab. Eng.*, (2001) 3:40-48.

Macherla, et al., "Structure-Activity Relationship Studies of Salinosporamide A (NPI-0052), a Novel Marine Derived Proteasome Inhibitor," *J. Med. Chem.*, (2005) 48(11): 3684-3687.

Manam et al., Leaving Groups Prolong the Duration of 20S Proteasome Inhibition and Enhance the Potency of Salinosporamide, J Med Chem., (Oct. 2008) 51(21): 6711-6724.

Manchand, et al., "Syntheses of the Anti-AIDS Drug 2',3'-Dideoxycytidine from Cytidine," *J. Org. Chem.*, (1992) 57:3473-3478.

Mayer, et al., "Efficacy of a Novel Hydrogel Formulation in Human Volunteers," *Ophthalmologica*, (1996) 210(2):101-103.

Mayer, et al., "Marine Pharmacology in 1999: Antitumor and Cytotoxic Compounds," *Anticancer Res.*, (2001) 21:2489-2500.

McMurry, John, *Organic Chemistry*, 5th ed., Brooks/Cole, Pacific Grove, CA. (2000), Chapter 11.5, pp. 398-408.

Meng, et al., "Eponemycin Exerts its Antitumor Effect Through the Inhibition of Proteasome Function," *Cancer Res.*, (1999), 59(12):2798-2801.

Meng, et al., "Epoxomicin, a Potent and Selective Proteasome Inhibitor, Exhibits In Vivo Anti-Inflammatory Activity," *Proc. Natl. Acad. Sci. USA*, (Aug. 1999) 96:10403-10408.

Merriam-Webster Online Dictionary, "Heteroatom", 2010, Merriam-Webster Online, accessed Jun. 16, 2010, http://merriam-webster.com/dictionary/heteroatom.

Min, et al., "Urokinase Receptor Antagonists Inhibit Angiogenesis and Primary Tumor Growth in Syngeneic Mice," *Cancer Res.*, (May 15, 1996) 56(10):2428-2433.

Mincer, et al., "Widespread and Persistent Populations of a Major New Marine Actinomycete Taxon in Ocean Sediments," *Applied and Environmental Microbiology*, (Oct. 2002) 68(10):5005-5011.

Mogridge, et al., "Stoichiometry of Anthrax Toxin Complexes," *Biochemistry*, (2002) 41:1079-1082.

Momose, et al., "2(3H)-and 2(5H)-Furanones. VII. Chirality Transfer on the Tetronic Acid Templates," *Heterocycles*, (1999) 51(6):1321-1343.

Moore, B.S., "Biosynthesis of Marine Natural Products: Microorganisms and Macroalgae," *Nat. Prod. Rep.*, (1999) 16(6):653-674.

Moran, et al., "Evidence for Indigenous *Streptomyces* Populations in Marine Environment Determined with a 16S rRNA Probe," *Applied and Environmental Microbiology*, (Oct. 1995) 61(10):3695-3700.

Mordenti, et al., "Intracular Pharmacokinetics and Safety of a Humanized Monoclonal Antibody in Rabbits after Intravitreal Administration of a Solution or a PLGA Microsphere Formulation," *Toxicol. Sci.*, (1999) 52(1):101-106.

Mousa, et al., "Angiogenesis Inhibitors: Current & Future Directions," *Current Pharmaceutical Design*, (2004) 10:1-9.

Mulholland et al., "A Concise Total Synthesis of Salinosporamide A," *Org. Biomol. Chem.*, (2006) 4: 2845-6.

Murray, J. Clifford (Ed.), *Angiogenesis Protocols (Methods in Molecular Medicine)*, Humana Press, Totowa, NJ. (2001) Table of Contents, p. 4.

Mutomba, et al., "Inhibition of Proteasome Activity Blocks Cell Cycle Progression at Specific Phase Boundaries in African Trypanosomes", *Mol. Biochem. Parasitology*, (1997) 90:491-504.

NCBI website, sequence for AB242910, http://www.ncbi.nlm.nih.gov/entrez/viewerfcgi?db=nucleotide&val=124300751, 2 pages, downloaded Feb. 15, 2007, 2 pages.

NCBI website, sequence for EF105548, http://www.ncbi.nlm.nih.gov/entrez/viewer.fcgi?db=nucleotide&val=118640518, 2 pages, downloaded Feb. 15, 2007, 2 pages.

NCBI website, Sequence for EF191171, http://www.ncbi.nlm.nih.gov/entrez/viewer.fcgi?db=nucleotide&val=124014014, 2 Pages, downloaded Feb. 15, 2007, 2 pages.

Nesterneko, et al., "*Rhodococcus luteus* nom. nov., and *Rhodococcus maris* nom. nov.", *Int'l Journal of Systematic Bacteriology*, (Jan. 1982) 32(1):1-14.

Newton. "Il fondo agli oceani potenti antibiotici e anticancro." www.newton.rcs.it/PrimoPiano/News/2003/02_Febbraio/03/Antobiotico.html. (Feb. 2, 2003) 1 page.

Nicholson, D.W., "ICE/CED 3-Like Proteases as Therapeutic Targets for the Control of Inappropriate Apoptosis," *Nat. Biotechnology*, (1996) 14:297-301.

(56) References Cited

OTHER PUBLICATIONS

Nicolaus B.J. R. "Symbiotic Approach to Drug Design," *Decision Making in Drug Research*, (1983) 173-186.

Nicosia, et al., "Growth of Microvessels in Serum-Free Matrix Culture of Rat Aorta: A Quantitative Assay of Angiogenesis In Vitro," *Laboratory Investigation*, (Jul. 1990) 63(1):115-122.

Nolan, et al., "Isolation and Screening of Actinomycetes," *Actinomycetes in Biotechnology*, (1988) Chapter 1:1-32.

O'Donnel, Anthony G., "Recognition of Novel Actinomycetes," *Actinomycetes in Biotechnology*, Academic Press, (1988) Chapter 3:69-88.

Oikawa, et al., "Angiogenic Factor of a Rat Mammary Tumor Cell Line (RMT-1) (I). Secretion of Two Distinct Angiogenic Factors into Serum-Free Conditioned Medium by RMT-1 Cells," *Cancer Letters*, (1991) 59:57-66.

Okami, Y., "The Search for Bioactive Metabolites from Marine Bacteria," *J. Marine Biotechnology*, (1993) 1: 59-65.

Omura, et al., "Lactacystin, A Novel Microbial Metabolite, Induces Neuritogenesis of Neuroblastoma Cells," *J. Antibiotics*, (1991) 44(1): 113-116.

O'Neil et al. eds., "The Merck Index," 13th Ed. 2001, Merck Research Laboratories, Whitehouse Station N.J., pp. THER-5-THER-7.

Online URL:http://web.archive.org/web/20060117081111/hivhep.tempdonnainname.com/hiv and aids/norvir effects . . . Nov. 22, 2010. 1 page.

Online www.netdoctor.co.uk "Isoniazid: Treatment of Tuberculosis", [accessed on Apr. 8, 2008] pp. 1-2.

Ostrowska, et al., "Lactacystin, A Specific Inhibitor of the Proteasome, Inhibits Human Platelet Lysosomal Cathepsin A-like Enzyme," *Biochem. Biophys. Res. Commun.*, (1997) 234:729-732.

Ostrowska, et al., "Separation of Cathepsin A-like Enzyme and the Proteasome: Evidence that Lactacystin/β-Lactone is not a Specific Inhibitor of the Proteasome," *Int. J. Biochem. Cell Biol.*, (2000) 32:747-757.

Otoguro, et al., "An intergrated method for the enrichment and selective isolation of *Actinokineospora* spp. in soil and plant litter," *J. Appl. Microbiol.*, (2001) 92:118-130.

Pagano, et al., "Role of the Ubiquitin-Proteasome Pathway in Regulating Abundance of the Cyclin-Dependent Dependent Kinase Inhibitor p27," *Science*, (1995) 269(5224):682-685.

Page, Roderic D.M., "TreeView: An Application to Display Phylogenetic Trees on Personal Computers," *Computer Applications in the Biosciences*, (1996) 12:357-358.

Painter, Robert B., "Inhibition of DNA Replicon Initiation by 4-Nitroquinoline 1-Oxide, Adriamycin, and Ethyleneimine," *Cancer Res.*, (1978) 38(12):4445-4449.

Palayoor, et al., "Constitutive Activation of IκB Kinase α and NF-κB in Prostate Cancer Cells is Inhibited by Ibuprofen," *Oncogene*, (1999) 18:7389-7394.

Peckham et al. (Eds.), "The Oxford Textbook of Oncology," *Oxford University Press*, Oxford (1995) vol. 1:447-453.

Pieters et al., "Microbiology: Chemical Warfare and Mycobacterial Defense", *Science*, (Dec. 2003) 302:1900-1902.

Plunkett, et al., "Methods in Laboratory Investigation: An In Vivo Quantitative Angiogenesis Model Using Tumor Cells Entrapped in Alginate," *Laboratory Investigation*, (Apr. 1990) 62(4):510-517.

Prudhomme et al., "Marine Actinomycetes: A New Source of Compounds against the Human Malaria Parasite," *Plos One*, (2008) 3(6): 1-8.

Qureshi, et al., "The Proteasome as a Lipopolysaccharide-Binding Protein in Macrophages: Differential Effects of Proteasome Inhibition on Lipopolysaccharide-Induced Signaling Events," *J. Immunol.*, (2003) 171(3):1515-1525.

Rappe, et al., "Cultivation of the Ubiquitous SAR11 1 Marine Bacterioplankton Clade," *Nature*, (Aug. 8, 2002) 418:630-633.

Reddy, et al., "A Simple Stereocontrolled Synthesis of Salinosporamide A," *J. Am. Chem. Soc.*, (2004) 126(20):6230-6231.

Reed et al., "Salinosporamides D-J from the Marine Actinomycete *Salinispora tropica*, Bromosolinosporamide, and Thioester Derivatives Are Potent Inhibitors of the 20S Proteasome", *J Nat Prod.*, (2007) 70: 269-276.

Riva, S., "Biocatalytic Modification of Natural Products," *Curr. Opin. Chem. Biol.*, (2001) 5:106-111.

Roche, Edward B. (Ed.), "Bioreversible Carriers in Drug Design: Theory and Application," Pergamon Press, Elmsford, NY (1987), pp. 14-21.

Rockwell, et al., "Proteasome Inhibition in Neuronal Cells Induces a Proinflammatory Response Manifested by Upregulation of Cyclooxygenase-2, Its Accumulation as Ubiquitin Conjugates, and Production of the Prostaglandin $PGE_2$," *Arch. Biochem. and Biophysics*, (2000) 374(2):325-333.

Romero, et al., "Thiocoraline, a New Depsipeptide with Antitumor Activity Produced by a Marine *Micromonospora*," *J. Antibiotics*, (1997) 50(9):734-737.

Rubanyi, Gabor M., "Angiogenesis in Health and Disease: Basic Mechanisms and Clinical Applications", *Marcel Dekker*, New York, NY (1999) pp. 6 Content Pages Only.

Ruiz, et al., "The Proteasome Inhibitor NPI-0052 is a More Effective Inducer of Apoptosis than Bortezomib in Lymphocytes from Patients with Chronic Lymphocytic Leukemia," *Mol. Cancer Ther.*, (2006) 5(7): 1836-1843.

Sapi, et al., "Simple and Condensed β-Lactam. Part 32. Base- and Acid-Catalyzed Ring Expansions of 3-Substituted 4-Acetylazetidin-2-ones and Related Compounds". *Collect. Czech. Chem. Commun.* (1999) 64(2):190-202.

Saravanan, et al., "A Short, Stereocontrolled, and Practical Synthesis of α-Methylomuralide, a Potent Inhibitor of Proteasome Function," *J. Org. Chem.*, (2003) 68(7):2760-2764.

Sausville et al., "Contributions of human tumor xenografts to anticancer drug development", *Cancer Res.* (2006) 66(7): 3351-3354.

Schiewe, H. (Reprint) Haustedt, et al., "Rational approaches to natural-product-based drug design", *Curr Opin Drug Disc Devel.* (2006) 9(4):445-462.

Schnaper, et al., "Plasminogen Activators Augment Endothelial Cell Organization In Vitro by Two Distinct Pathways," *J. Cell. Physiol.*, (1995) 165:107-118.

Shadomy, et al., "Antimycotic and Antirickettsial," *Antibiotics, Chemotherapeutics, and Antibacterial Agents for Disease Control*, Martin Grayson (Ed.) John Wiley and Sons, New York (1982) 371-395.

Shah, et al., "Early Clinical Experience With the Novel Proteasome Inhibitor PS-519," *J. Clin. Phatmacol.*, (2002) 54:269-276.

Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicenter Study," *Clin. Ther.*, (2001) 23(3):440-450.

Shimada, et al., "Contributions of Mitogen-Activated Protein Kinase and Nuclear Factor Kappa B to N-(4-hydroxyphenyl) Retinamide-Induced Apoptosis in Prostate Cancer Cells," *Molecular Carcinogenesis*, (2002) 35(3):127-137.

Shoemaker, R., "The NCI60 Human Tumour Cell Line Anticancer Drug Screen," *Nature Reviews Cancer*, (2006) 6:813-823.

Silva-Jardim, et al., "The *Leishmania chagasi* Proteasome: Role in Promastigotes Growth and Amastigotes Survival within Murine Macrophages", *Acta Tropica*, (2004) 91:121-130.

Silverman, Richard B., *The Organic Chemistry of Drug Design and Drug Action*, Academic Press, San Diego, (1992) 19-21.

Stach, et al., "New Primers for the Class *Actinobacteria*: Application to Marine and Terrestrial Environments," *Environmental Mircrobiology*, (2003) 5(10):828-841.

Stach, et al., "Statistical Approaches for Estimating Actinobacterial Diversity in Marine Sediments," *Appl. Environ.I Mircrobiol.*, (Oct. 2003) 69(10):6189-6200.

Stackebrandt, et al., "Proposal for a New Hierarchic Classification Systems, *Actinobacteria* classis Nov.," *Int. J. of Syst. Bacteriol.*, (Apr. 1997) 47(2):479-491.

(56) References Cited

OTHER PUBLICATIONS

Stackebrandt, et al., "Taxonomic Note: A Place for DNA-DNA Reassociation and 16S rRNA Sequence Analysis in the Present Species Definition in Bacteriology," *Int. J. of Syst. Bacteriol.*, (Oct. 1994) 44(4):846-849.

Stadler et al., "Cinnabaramides A-G: Analogues of Lactacystin and Salinosporamide from a Terrestrial Streptomycete," *J. Nat. Prod.* (Feb. 2007) 70(2):246-252.

Stanford, et al., "Bortezomib Treatment for Multiple Myeloma," *Ann. Pharmacother.*, (2003) 37:1825-1830.

Stella et al., (Ed.), "Prodrugs: Challenges and Rewards, Part 1", American Association of Pharma. Scientists (2007), p. 24.

Streitwieser et al., *Introduction to Organic Chemistry*, 2nd ed., Macmillan Publishing Co. Inc., New York, NY (1981) pp. 169-171.

Sunwoo, et al., "Novel Proteasome Inhibitor PS-341 Inhibits Activation of Nuclear Factor-kB, Cell Survival, Tumor Growth, and Angiogenesis in Squamous Cell Carcinoma," *Clin. Cancer Res.*, (2001) 7:1419-1428.

Tabuchi, et al., "Application of 'Proteasome Tolerance' to Therapies for Neurodegenerative Disease," *Alzheimer's and Dementia*, (2006) 2(3) (1 Supplement):S628.

Takeuchi, et al., "Troglitazone Induces G1 Arrest by p27 Induction That Is Mediated by Inhibition of Proteasome in Human Gastric Cancer Cells," *Jpn. J. Cancer Res.*, (2002) 93:774-782.

Tang, et al., "Cloning and Hererologous Expression of the Epothilong Gene Cluster," *Science*, (Jan. 28, 2000) 287:640-642.

Tang, et al., "Proteasome Activity is Required for Anthrax Lethal Toxin to Kill Macrophages," *Infect. Immun.*, (1999) 67(6):3055-3060.

Tauchi, et al., "Molecular Mechanisms of Resistance of Leukemia to Imatinib Mesylate," *Leukemia Research*, (May 2004) 28:39-45.

Thompson, et al., "Clustal W: improving the sensitivity of progressive multiple sequence alignment through sequence weighting, position-specific gap penalties and weight matrix choice," *Nucleic Acids Research*, (1994) 22(22):4673-4680.

Versalovic, et al., "Distribution of repetitive DNA sequences in eubacteria and application to fingerprinting of bacterial genomes," *Nucleic Acids Research*, (1991) 19(24):6823-6831.

Vitale, et al., "Anthrax lethal factor cleaves the N-terminus of MAPKKS and induces tyrosine/threonine phosphorylation of MAPKS in cultured macrophages," *J. Applied Microbiology*, (1999) 87:288.

Vitale, et al., "Susceptibility of Mitogen-Activated Protein Kinase Kinase Family Members to Proteolysis by Anthrax Lethal Factor," *Biochem. J.*, (2000) 352:739-745.

Voskoglou-Nomikos, et al., "Clinical Predictive Value of the in Vitro Cell Line, Human Xenograft, and Mouse Allograft Preclinical Cancer Models", *Clin Cancer Res.*, (2003) 9:4227-4239.

Ward, Bess B., "How Many Species of Prokaryotes are There?" *Proc. Natl. Acad. Sci. USA*, (Aug. 6, 2002) 99(16):10234-10236.

Watve, et al., "How Many Antibiotics are Produced by the Genus *Streptomyces?*" *Arch. Microbio.*, (2001) 176:386-390.

Weyland, H., "Actinomycetes in North Sea and Atlantic Ocean Sediments," *Nature*, (1969) 223:858.

Weyland, H., "Distribution of Actinomycetes on the Sea Floor," *Actinomycetes ZBL. Bakt. Suppl.*, (1981) 11:185-193.

Wheelis, et al., "On the Nature of Global Classification," *Proc. Natl. Acad. Sci. USA*, (Apr. 1992) 89:2930-2934.

Williams et al., "New Cytotoxic Salinosporamides from the Marine Actinomycete *Salinispora tropica*," *J. Org. Chem.*, (2005) 70(16):6196-6203.

Woese, Carl R., "Bacterial Evolution," *Microbiological Rev.*, (Jun. 1987) 51(2):221-271.

Yew, et al., "Proteasome Inhibition by Lactacystin in Primary Neuronal Cells Induces Both Potentially Neuroprotective and Pro-Apoptotic Transcriptional Responses: a Microarray Analysis," *J. Neurochem.*, (2005) 94(4):943-956.

Zaks, A., "Industrial Biocatalysis," *Curr. Opin. Chem. Biol.*, (2001) 5:130-136.

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia," *Stroke*, (2001) 2926-2931.

Zheng, et al., "Detection of Antitumor and Antimicrobial Activities in Marine Organism Associated Actinomycetes Isolated From the Taiwan Strait, China," *FEMS Microbiology Letters*, (2000) 188:87-91.

International Search Report and Written Opinion dated Jul. 12, 2006 in International Application No. PCT/US2005/044091, International Filing Date: Dec. 2, 2005.

International Preliminary Report on Patentability dated Jun. 14, 2007 in International Application No. PCT/US2005/044091, International Filing Date: Dec. 2, 2005.

International Search Report and Written Opinion (corrected version) dated Jul. 8, 2005 in International Application No. PCT/US2004/019543, International Filing Date: Jun. 18, 2004.

International Preliminary Report on Patentability dated Jan. 3, 2006 in International Application No. PCT/US2004/019543, International Filing Date: Jun. 18, 2004.

International Search Report and Written Opinion dated Nov. 29, 2004 in International Application No. PCT/US2004/019453, International Filing Date: Jun. 18, 2004.

International Preliminary Report on Patentability dated Mar. 14, 2005 in International Application No. PCT/US2004/19453, International Filing Date: Jun. 18, 2004.

International Search Report and Written Opinion dated Dec. 29, 2006 in International Application No. PCT/US2005/014846, International Filing Date: Apr. 29, 2005.

International Preliminary Report on Patentability dated Jan. 23, 2007 in International Application No. PCT/US2005/014846, International Filing Date: Apr. 29, 2005.

International Search Report dated Aug. 2, 2002 in International Application No. PCT/US01/043758, International Filing Date: Nov. 16, 2001.

International Preliminary Report on Patentability dated Aug. 24, 2004 in International Application No. PCT/US2001/043758, International Filing Date: Nov. 16, 2001.

International Search Report and Written Opinion dated Feb. 27, 2007 in International Application No. PCT/US06/016104, International Filing Date: Apr. 27, 2006.

International Preliminary Report on Patentability dated Oct. 30, 2007 in International Application No. PCT/US2006/016104, International Filing Date: Apr. 27, 2006.

International Search Report and Written Opinion mailed Jan. 29, 2009 for corresponding International Application No. PCT/US2008/062553 International Filing Date: May 2, 2008.

International Preliminary Report on Patentability dated Nov. 19, 2009 in International Application No. PCT/US2008/062553, International Filing Date: May 2, 2008.

International Search Report and Written Opinion dated Sep. 28, 2009 for International Application No. PCT/US2009/043644, International Filing Date: May 12, 2009.

International Preliminary Report on Patentability (Chapter II) dated Aug. 6, 2010 for International Application No. PCT/US2009/043644, International Filing Date: May 12, 2009.

International Search Report and Written Opinion dated May 12, 2006 in International Application No. PCT/US2005/043668, International Filing Date: Dec. 2, 2005.

International Preliminary Report on Patentability dated Jun. 14, 2007 in International Application No. PCT/US2005/043668, International Filing Date: Dec. 2, 2005.

International Search Report and Written Opinion dated Nov. 15, 2005 in International Application No. PCT/US2005/012218, International Filing Date: Apr. 11, 2005.

International Preliminary Report on Patentability dated Oct. 11, 2006 in International Application No. PCT/US2005/012218, International Filing Date: Apr. 11, 2005.

International Search Report and Written Opinion dated Oct. 19, 2005 in International Application No. PCT/US2005/012113, International Filing Date: Apr. 11, 2005.

International Preliminary Report on Patentability dated Oct. 11, 2006 in International Application No. PCT/US2005/012113, International Filing Date: Apr. 11, 2005.

(56) References Cited

OTHER PUBLICATIONS

International Search Report and Written Opinion dated Jan. 10, 2007 in International Application No. PCT/US2006/031314, International Filing Date: Aug. 10, 2006.
International Preliminary Report on Patentability dated Feb. 12, 2008 in International Application No. PCT/US2006/031314, International Filing Date: Aug. 10, 2006.
International Search Report and Written Opinion dated Aug. 3, 2007 in International Application No. PCT/US2006/035196, International Filing Date: Sep. 8, 2006.
International Preliminary Report on Patentability dated Mar. 18, 2008 in International Application No. PCT/US2006/035196, International Filing Date: Sep. 8, 2006.
EFS File History of U.S. Appl. No. 10/871,368, filed Mar. 3, 2005.
EFS File History of U.S. Appl. No. 12/136,688, filed Jun. 10, 2008 as of Jan. 20, 2011.
EFS File History of U.S. Appl. No. 11/118,260, filed Apr. 29, 2005.
EFS File History of U.S. Appl. No. 09/991,518, filed Nov. 16, 2001.
EFS File History of U.S. Appl. No. 11/228,416, filed Sep. 15, 2005.
EFS File History of U.S. Appl. No. 11/841,588, filed Aug. 20, 2007.
EFS File History of U.S. Appl. No. 11/966,787, filed Dec. 28, 2007.
EFS File History of U.S. Appl. No. 11/966,801, filed Dec. 28, 2007 as of Mar. 24, 2011.
EFS File History of U.S. Appl. No. 10/600,854, filed Jun. 20, 2003.
EFS File History of U.S. Appl. No. 10/838,157, filed Apr. 30, 2004.
EFS File History of U.S. Appl. No. 11/147,622, filed Jun. 7, 2005.
EFS File History of U.S. Appl. No. 11/705,694, filed Feb. 12, 2007.
EFS File History of U.S. Appl. No. 12/638,860, filed Dec. 15, 2009 as of May 16, 2011.
EFS File History of U.S. Appl. No. 11/412,476, filed Apr. 27, 2006.
EFS File History of U.S. Appl. No. 11/865,704, filed Oct. 1, 2007.
EFS File History of U.S. Appl. No. 11/453,374, filed Jun. 15, 2006.
EFS File History of U.S. Appl. No. 12/114,449, filed May 2, 2008.
EFS File History of U.S. Appl. No. 12/464,686, filed May 12, 2009.
EFS File History of U.S. Appl. No. 11/293,354, filed Dec. 2, 2005.
EFS File History of U.S. Appl. No. 10/821,621, filed Apr. 9, 2004.
EFS File History of U.S. Appl. No. 11/539,648, filed Oct. 9, 2006.
EFS File History of U.S. Appl. No. 12/028,024, filed Feb. 8, 2008.
EFS File History of U.S. Appl. No. 11/224,589, filed Sep. 12, 2005.

\* cited by examiner

COMPOSITIONS AND METHODS FOR TREATING NEOPLASTIC DISEASES

CROSS-REFERENCE TO RELATED APPLICATIONS

This application is a continuation of U.S. application Ser. No. 11/293,354, filed Dec. 2, 2005, now abandoned, which claims the benefit of U.S. Provisional Application No. 60/633,161, filed Dec. 3, 2004, both of which are incorporated herein by reference in their entirety.

STATEMENT OF GOVERNMENT INTEREST

The work described herein was partially funded by NIH grants 50947, CA 78373, SPORE P50 CA100707-01, and P01 CA078378-06 and the U.S. government may have certain rights with regard to the present invention.

BACKGROUND OF THE INVENTION

1. Field of the Invention

The present invention relates to the fields of chemistry and medicine. More particularly, the present invention relates to the treatment of neoplastic diseases, such as cancer.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent.

Therefore, a need exists for additional chemotherapeutics to treat cancer. A continuing effort is being made by individual investigators, academia and companies to identify new, potentially useful chemotherapeutic and anti-microbial agents.

The successful development of Bortezomib/PS-341 therapy for treatment of relapsed/refractory multiple myeloma (MM) has established proteasome inhibition as an effective therapeutic strategy. The dipeptide boronic acid analogue Bortezomib is a potent, highly selective, and reversible proteasome inhibitor which targets the 26S proteasome complex and inhibits its function. The 26S proteasome is an adenosine triphosphate (ATP)-dependent multicatalytic protease mediating intracellular protein degradation. Proteasomal degradation of misfolded or damaged proteins proceeds by recognition of polyubiquitinated proteins by the 19S regulatory subunit of the 26S protease, and subsequent hydrolysis to small polypeptides. Bortezomib primarily inhibits chymotryptic, without altering tryptic or caspase-like, proteasome activity. Besides inhibiting NF-kB, Bortezomib has pleiotropic effects on MM biology by targeting: 1) cell-cycle regulatory proteins; 2) UPR pathway via modulating transcriptional activity of plasma cell differentiation factor X-box binding protein-1 (XBP-1); 3) p53-mediated apoptosis/MDM2; 4) DNA repair mechanisms; 5) classical stress-response pathways via both intrinsic (caspase-9 mediated) and extrinsic (caspase-8 mediated) cell death cascades. Specifically, Bortezomib activates JNK, which triggers mitochondrial apoptotic signaling: release of cytochrome-c (cyto-c) and second mitochondrial activator of caspases (Smac) from mitochondria to cytosol, followed by activation of caspase-9 and caspase-3. However, both intrinsic and acquired resistance has already been observed, and there are no therapies to overcome Bortezomib resistance at present.

SUMMARY OF THE INVENTION

One aspect of the present invention is a method of treating a neoplastic disease, comprising administering to a patient inflicted with the neoplastic disease a compound of formula (I) or a pharmaceutically acceptable salt or prodrug thereof:

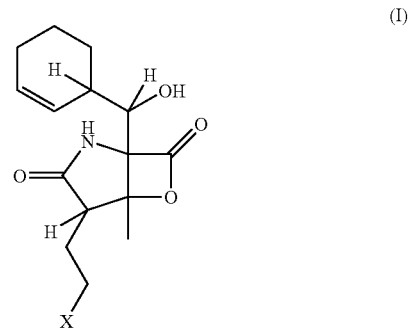

wherein X is selected from the group consisting of fluorine, chlorine, bromine or iodine, and wherein the neoplastic disease is susceptible to resistance to at least one other chemotherapeutic agent.

Another aspect of the present invention is a method of treating a neoplastic disease, comprising administering to a patient inflicted with the neoplastic disease a compound of formula (I) or a pharmaceutically acceptable salt or prodrug thereof wherein X is selected from the group consisting of fluorine, chlorine, bromine or iodine, in combination with at least one additional chemotherapeutic agent.

Another aspect of the present invention is a pharmaceutical composition, comprising a compound of formula (I) or a pharmaceutically acceptable salt or prodrug thereof, wherein X is selected from the group consisting of fluorine, chlorine, bromine or iodine, and at least one additional chemotherapeutic agent.

Another aspect of the present invention is a method of treating a neoplastic disease, comprising administering to a patient inflicted with the neoplastic disease a synergistic combination of at least two proteosome inhibitors.

DETAILED DESCRIPTION OF THE PREFERRED EMBODIMENT

Figure 1:
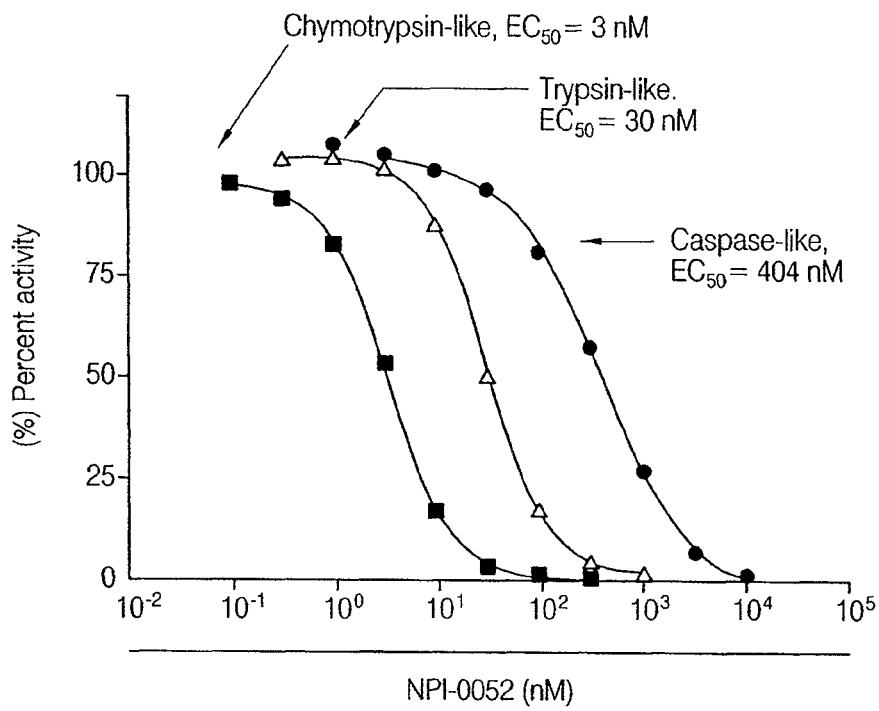
FIG. 1 illustrates inhibition of chymotrypsin-like, caspase-like, and trypsin-like proteasome activities in human erythrocytes-derived 20S proteasome by NPI-0052.

In one embodiment, a compound according to formula (I) is provided for use as described herein:

(I)

where X may be fluorine, chlorine, bromine or iodine. In one embodiment, X is chlorine. In one embodiment, the compound of formula (I) has stereochemistry according to formula (II):

(II)

The compound of formula (II) where X=Cl is also referred to herein as NPI-0052. Compounds according to formulae (I) or (II) may be derived from fermentation of Salinospora, a marine gram-positive actinomycete.

In some embodiments, prodrugs, metabolites, stereoisomers, and pharmaceutically acceptable salts of the compounds disclosed herein are provided for use as described herein.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

Metabolites of the compounds disclosed herein include active species that are produced upon introduction of the compounds into the biological milieu.

Where the compounds disclosed herein have at least one chiral center, they may exist as a racemate or as enantiomers. It should be noted that all such isomers and mixtures thereof are included in the scope of the present invention. Furthermore, some of the crystalline forms for the compounds of disclosed herein may exist as polymorphs. Such polymorphs are included in one embodiment of the present invention. In addition, some of the compounds of the present invention may form solvates with water (i.e., hydrates) or common organic solvents. Such solvates are included in one embodiment of the present invention.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein can be used alone, in combination with other compounds disclosed herein, or in combination with one or more other agents active in the therapeutic areas described herein.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein in its entirety.

The terms "purified," "substantially purified," and "isolated" as used herein refer to compounds disclosed herein being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

Methods of Use

As demonstrated by the examples presented herein, the compound of formula (I) inhibits chymotrypsin-like, trypsin-like, and caspase-like proteasome activities. In contrast, Bortezomib has been shown to inhibit only chymotrypsin-like proteasome activity. See Goldberg, A. L. & Rock, K. (2002) *Nat Med* 8, 338-40 and Adams, J. (2004) *Nat Rev Cancer* 4, 349-60; both of which are incorporated herein by reference in their entirety. It is further demonstrated that compounds of formula (I) have a different mechanism of action than bortezomib. Furthermore, the compound of formula (I) induces apoptosis in various multiple myeloma cell lines including, but not limited to, Dexamethasone-sensitive MM.1S, Dexamethasone-resistant MM.1R, RPMI-8226, OPM2, U266, and Doxorubicin-resistant Dox-40. The compound of formula I also induced apoptosis in cell lines obtained from human multiple myeloma patients that had relapsed after multiple prior therapies with Dexamethasone, Bortezomib, and thalidomide. Thus, the compound of formula (I) is effective against MM cells that are resistant to other chemotherapeutic agents, including Dexamethasone, Doxorubicin, Bortezomib/PS-341, and thalidomide.

Accordingly, in one embodiment, a method of treating a neoplastic disease that is susceptible to resistance to at least one chemotherapeutic agent is provided comprising administering to a patient, such as a human, a compound of formula (I) or a pharmaceutically acceptable salt or prodrug ester thereof. By "resistance to at least one chemotherapeutic agent," it is meant that administration of the chemotherapeutic agent to the patient does not result in significant amelioration of symptoms of the neoplastic disease. In some embodiments where the neoplastic disease is a characterized by a tumor, "resistance to at least one chemotherapeutic agent" means that administration of the chemotherapeutic agent does not result in appreciable inhibition of the growth of the tumor or reduction in the size of the tumor. "Resistance to at least one chemotherapeutic agent" can also mean that when the agent is exposed to resistant tumor cells, no appreciable apoptosis is induced. By "susceptible to" resistance to at least one chemotherapeutic agent, it is meant that the neoplastic disease currently is resistant to the at least one chemotherapeutic agent or will develop resistance upon repeated administration of the chemotherapeutic agent.

The examples herein also demonstrate that compounds of formula (I) when combined with bortezomib trigger synergistic apoptosis in MM cells. Thus, a compound of formula (I) may be administered in combination with Bortezomib/PS-341 to achieve apoptosis using lower doses of each agent than if the agents were administered separately, thus reducing the toxicity of the agents. Surprisingly, these results demonstrate that a synergistic result may be obtained by administering two different proteasome inhibitors. By "synergistic," it is meant that the combination of two or more agents yield a combination index (CI)<1.0. It has also been demonstrated that combination of the compound of formula (I) with non-proteasome inhibitor agents provide an additive effect. By "additive," it is meant that the combination of two or more agents yield a CI approximately equal to one. CI may be determined, for example, by the Chou-Talalay method according to the following equation: "CI=(D)1/(Dx)1+(D)2/(Dx)2+(D)1(D)2/(Dx)1(Dx)2", where (D)1 and (D)2 are the doses of drug 1 and drug 2 that have x effect when used in combination; and (Dx)1 and (Dx)2 are the doses of drug 1 and drug 2 that have the same x effect when used alone.

Accordingly, in one embodiment, a method is provided for treating a neoplastic disease comprising administering two or more proteasome inhibitors in synergistic combination. Non-limiting examples of classes of proteasome inhibitors that may be combined include peptide boronate proteasome inhibitors, peptide aldehyde proteasome inhibitors, and non-peptide proteasome inhibitors. A non-limiting example of a peptide boronate proteasome inhibitor is bortezomib. A non-limiting example of a peptide aldehyde proteasome inhibitor is MG-132. Non-limiting examples of non-peptide proteasome inhibitors include omuralide and the compound of formula (I). In one embodiment, at least one of the proteasome inhibitors is a compound of formula (I) or bortezomib. By administration in "combination," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v. In one advantageous embodiment, the pharmacokinetics of the two or more agents are substantially the same.

In one embodiment, a method is provided for treating a neoplastic disease comprising administering a compound of formula (I) in combination with another chemotherapeutic agent. In one embodiment, the other chemotherapeutic agent is dexamethasone, doxorubicin, or thalidomide. In one embodiment, the other chemotherapeutic agent is another proteasome inhibitor such as bortezomib. In one embodiment, a pharmaceutical composition is provided that combines a compound of formula (I) with the additional chemotherapeutic agent.

In some embodiments, the neoplastic disease treated by any of the methods above may be a cancer selected from breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer. In one embodiment, the neoplastic disease is a multiple myeloma.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound or combination disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound or combination of compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction.

Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Example 1

General Procedures

Cell Culture and Reagents.

Dex-sensitive MM.1S and Dex-resistant MM.1R human MM cell lines were obtained from Dr. Steven Rosen (Northwestern University, Chicago, Ill.). See Moalli, P. A., Pillay, S., Weiner, D., Leikin, R. & Rosen, S. T. (1992) Blood 79, 213-22 and Chauhan, D., Catley, L., Hideshima, T., Li, G., Leblanc, R., Gupta, D., Sattler, M., Richardson, P., Schlossman, R. L., Podar, K., Weller, E., Munshi, N. & Anderson, K. C. (2002) Blood 100, 2187-94; both of which are incorporated herein by reference in their entirety. RPMI-8226 and Doxorubicin (Dox)-resistant (Dox-40) cells were obtained from Dr. William Dalton (Moffit Cancer Center, Tampa, Fla.). U266 and OPM2 MM cell lines were obtained from the American Type Culture Collection (Rockville, Md.). The human tumor cell lines DU 145, HT-29, Jurkat, LoVo, MDA-MB-231, MIA PaCa-2, NCI-H292, OVCAR-3, PANC-1, and PC-3 were purchased from ATCC (Manassas, Va.). MM Cell lines were grown in RPMI-1640 media supplemented with 10% heat inactivated fetal-bovine serum (FBS), 100 units/ml penicillin, 100 μg/ml streptomycin, and 2 mM L-glutamine. MM cells were freshly isolated from patients relapsing after multiple prior therapies including Dexamethasone (Dex), melphalan, thalidomide or Bortezomib. MM cells were purified from patient bone marrow samples by CD138 positive selection method using CD138 (Syndecan-1) Micro Beads and the Auto MACS magnetic cell sorter (Miltenyi Biotec Inc., Auburn, Calif.). See Chauhan, D., Catley, L., Hideshima, T., Li, G., Leblanc, R., Gupta, D., Sattler, M., Richardson, P., Schlossman, R. L., Podar, K., Weller, E., Munshi, N. & Anderson, K. C. (2002) Blood 100, 2187-94; which is incorporated herein by reference in its entirety. Normal human skin fibroblasts CCD-27sk were obtained from ATCC and grown in DMEM supplemented with 10% heat inactivated FBS, 100 units/ml penicillin, 100 μg/ml streptomycin, 4 mM L-glutamine and 1 mM sodium pyruvate. Cells were treated with various concentrations of the compound of formula II (X=Cl) (Nereus Pharmaceuticals, Inc, San Diego, Calif.), Bortezomib or Dex (Sigma Chemical Co, St. Louis, Mo.).

Cell Viability and Apoptosis Assays.

Cell viability was assessed by 3-(4,5-dimethylthiazol-2-yl)-2,5-diphenyltetrazolium bromide (MTT; Chemicon International Inc., Temecula, Calif.) assay, according to manufacturer's instructions (Roche Molecular Biochemicals, Indianapolis, Ind.), and as described in Chauhan, D., Catley, L., Hideshima, T., Li, G., Leblanc, R., Gupta, D., Sattler, M., Richardson, P., Schlossman, R. L., Podar, K., Weller, E., Munshi, N. & Anderson, K. C. (2002) Blood 100, 2187-94; which is incorporated herein by reference in its entirety. Cell Death Detection ELISAplus was utilized to quantitate cell death, as per manufacturer's instructions (Roche Applied Sciences, Indianapolis, Ind.).

Example 2

In Vitro 20S Proteasome Activity Assay

The chymotrypsin-like activity of the 20S proteasome was measured as described in Stein, R. L., Melandri, F. & Dick, L. (1996) Biochemistry 35, 3899-908 and Lightcap, E. S., McCormack, T. A., Pien, C. S., Chau, V., Adams, J. & Elliott, P. J. (2000) Clin Chem 46, 673-83; both of which are incorporated herein by reference in their entirety. Purified human erythrocyte-derived 20S proteasome were obtained from Biomol, Plymouth Meeting, Pa. The chymotrypsin-like, caspase-like and trypsin-like activity activities of the 20S proteasome were determined using Suc-LLVY-AMC, Z-LLE-AMC (Boston Biochem, Cambridge, Mass.) and Boc-LRR-AMC (Bachem Bioscience, King of Prussia, Pa.) as peptide substrates, respectively. Fluorescence of the cleaved peptide substrate was measured using a Fluoroskan Ascent 96-well microplate reader (Thermo Electron, Waltham, Mass.). The $EC_{50}$ values were calculated by Prism (GraphPad Software) using a sigmoidal dose-response, variable slope model. The $EC_{50}$ values were defined as the drug concentration at which 50% of the maximal relative fluorescence is inhibited. The results, plotted in FIG. 1, indicated that the compound of formula (II) (X=Cl) inhibits all three proteasome activities, albeit at different concentrations.

Example 3

Analysis of Ex Vivo 20S Proteasome Activity in Whole Blood Cells in Mice (Single I.V. or Oral Administration)

To directly determine whether the compound of formula (II) (X=Cl) inhibits proteasome activity in vivo, the compound of formula (II) (X=Cl) was dissolved in 100% DMSO and serially diluted with 5% Solutol (Solutol® HS 15; polyethylene glycol 660 12-hydroxystearate, BASF, Shreveport, La.) yielding a final concentration of 2% DMSO. The vehicle control consisted of 2% DMSO and 98% (5% Solutol® HS15). Male Swiss-Webster mice (five per group, 20-25 grams in weight) were treated at Bolder BioPATH, Inc. (Boulder, Colo.) with various concentrations of the compound either intravenously or orally at a volume of 10 mL/kg. One group of animals was untreated to establish a baseline of proteasome activity. Ninety minutes after administration of the compound, the animals were anesthetized and blood withdrawn by cardiac puncture. Packed whole blood cells were collected by centrifugation, washed with PBS, and frozen on dry ice for determination of ex vivo proteasome activity.

Figure 2:
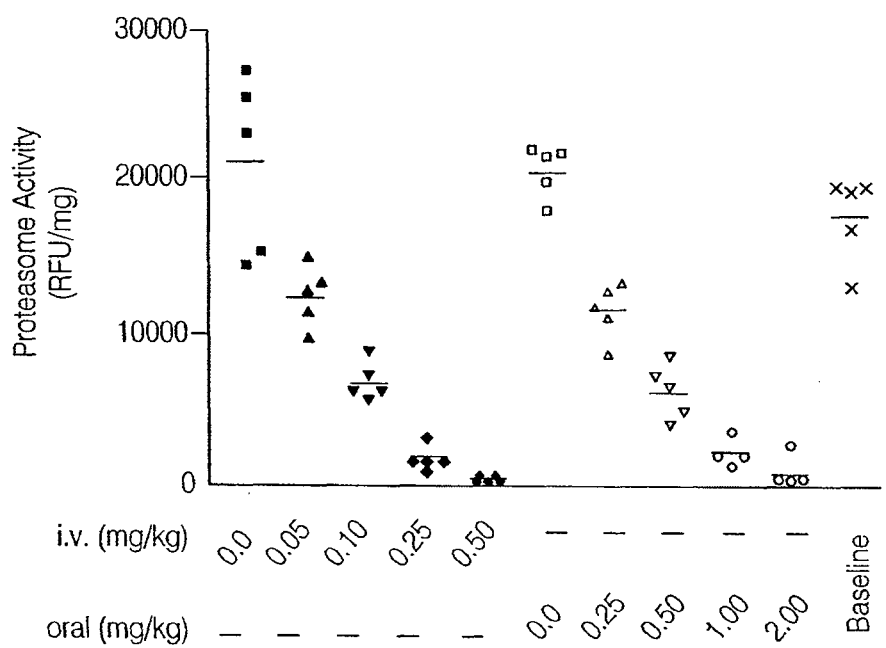
FIG. 2 illustrates the in vivo chymotrypsin-like activity of NPI-0052 in mice.

Chymotrypsin-like activity of the 20S proteasome in white blood cell (WBC) lysates was determined using the peptide substrate suc-LLVY-AMC. Relative Fluorescence Units (RFU) were normalized using the protein concentrations of the cell lysates. The 20S proteasome activity of the individual mice is shown in FIG. 2 with the horizontal bar representing the average activity. Baseline represents the 20S proteasome activity observed in WBC lysates prepared from untreated mice. The results, depicted in FIG. 2, indicate that the compound of formula (II) (X=Cl) inhibits chymotrypsin-like activity of 20S proteasomes in white blood cells in a dose-dependent manner. Importantly, these findings establish that the compound is orally active and inhibits proteasome activity in vivo.

Example 4

Determination of Triggered Alterations in Proteasome Activity in Mm Cells (In Vitro)

Figures 3, 4:
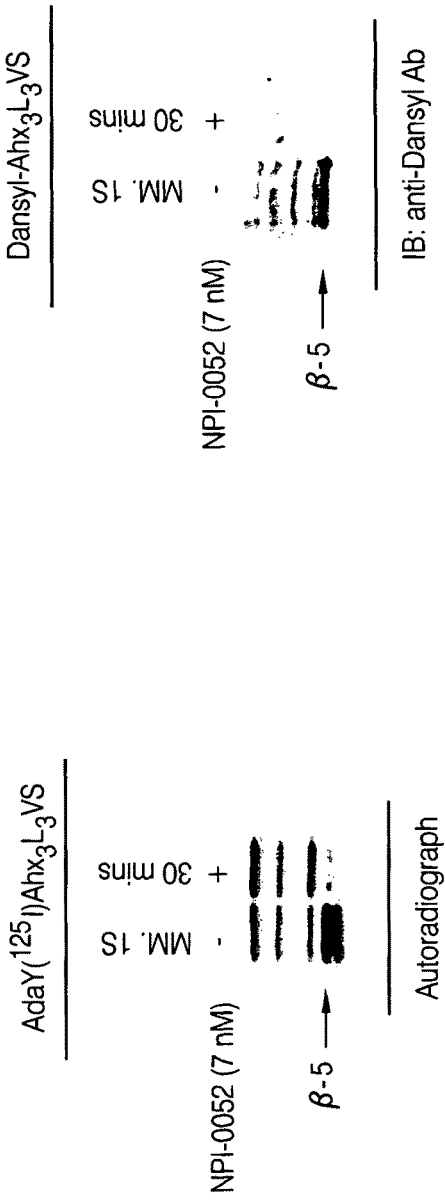
FIG. 3 depicts the autoradiograph obtained after treating MM.1S multiple myeloma (MM) cells with NPI-0052 (7 nM) and incubating protein extracts with AdaY($^{125}$I)Ahx$_3$L$_3$VS at 37° C.
FIG. 4 depicts immunoblots obtained after treating MM.1S cells with NPI-0052 and then incubating with Dansyl-Ahx3L3VS.

Determination of whether the compound of formula II (X=Cl) affects the proteasome activity in multiple myeloma cells in vitro was made using a competition experiment with AdaY$^{125}$Iahx$_3$L$_3$VS. In this assay, sites that are not targeted by the compound of formula II (X=Cl) are labeled by AdaY($^{125}$I)Ahx$_3$L$_3$VS and visualized by autoradiography, while sites that are targeted by the compound of formula II (X=Cl) can not be seen on the autoradiogram. MM.1S MM cells were incubated with the compound of formula (II) (X=Cl) (7 nM) for 30 mins, 1 h, 3 h, or 6 h, and cell lysis was performed with glass beads. 60 µg of protein extracts was incubated for 2 h with the iodinated proteasome inhibitor AdaY$^{125}$Iahx$_3$L$_3$VS at 37° C. Proteins were then denatured by boiling in reducing sample buffer and separated on a 12.5% SDS-PAGE gel, followed by autoradiography. As can be seen in FIG. 3, the beta-5 (β-5) subunit of the proteasome is markedly less labeled by AdaY($^{125}$I)Ahx$_3$L$_3$VS in treated cells than control cells. Given that the β-5 subunit mediates the chymotrypsin-like activity, these results suggest that the compound of formula (II) (X=Cl) binds to the β-5 subunit, thereby inhibiting the chymotrypsin-like activity in MM.1S cells. Moreover, treatment of MM.1S cells with the compound (7 nM) for 6 h also decreased the labeling of the β-2 subunits (tryptic-activity) and the β-1 subunits (caspase-like activity) (data not shown).

Example 5

Determination of Triggered Alterations in Proteasome Activity in MM Cells (In Vivo)

In vivo determination of proteasome activity was conducted using a competition experiment with Dansyl-Ahx$_3$L$_3$VS, which covalently modifies all active proteasome subunits. This inhibitor contains a dansyl sulfonamide hexanoyl hapten that can be visualized by immunoblotting using antibodies against the dansyl moiety. MM.1S cells were treated with the compound of formula (II) (X=Cl) (7 nM) for 30 mins, 1 h, or 3 h, followed by 1 h incubation with 5 µM Dansyl-Ahx$_3$L$_3$VS at 37° C. Cells were lysed by incubating them for 30 mins in NP-40 lysis buffer (50 mM Tris-HCl pH 8.0, 150 mM NaCl, 1% NP-40), followed by 5 min. centrifugation to remove membrane fractions, nuclei, and cell debris. 60 µg of protein extract was separated by 12.5% SDS-PAGE gel, followed by Immunoblot analysis using polyclonal anti-dansyl polyclonal Ab (1:7500, rabbit, Molecular Probes) and horseradish peroxidase coupled goat anti-rabbit secondary antibody (Southern Biotech). Blots were developed by enhanced chemiluminescence (Western Lightning, Perkin-Elmer). As can be seen in FIG. 4, treatment of MM.1S cells with the compound of formula (II) (X=Cl) decreases the dansylAhx$_3$L$_3$VS-labeling of the β-5 subunits. Furthermore, the compound also decreased the dansylAhx$_3$L$_3$VS-labeling of the β-1 and β-2 subunits, albeit at higher concentrations: 1 nM and 20 nM, respectively. In contrast, treatment of MM.1S cells with even higher doses of Bortezomib does not inhibit the β-2 subunits (data not shown). Taken together, these findings demonstrate the ability of the compound of formula (II) (X=Cl) to inhibit all three proteasome activities in MM cells.

Example 6

Effect on MM Cell Viability

Figure 5B:
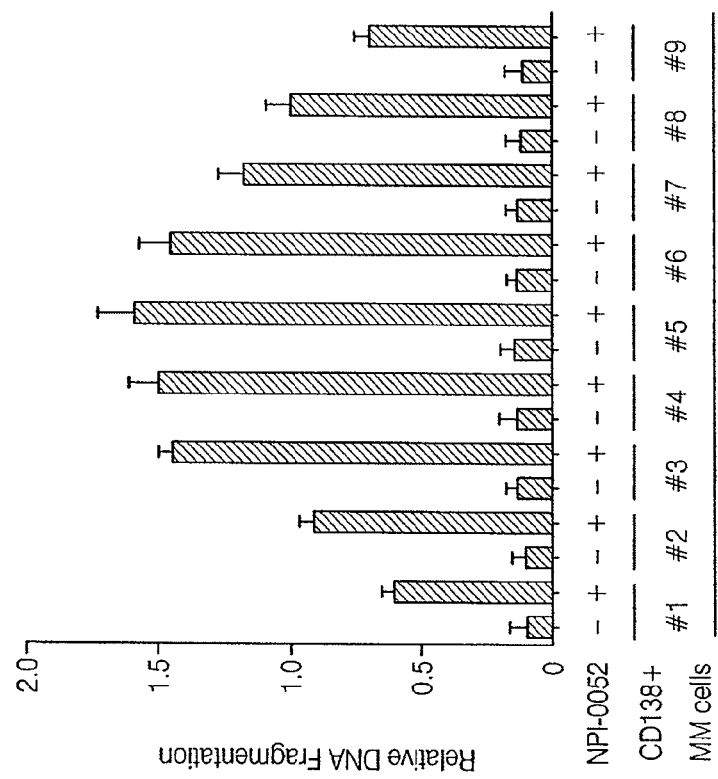
FIG. 5B illustrates DNA fragmentation assays of apoptosis after treatment with NPI-0052 of MM cells obtained from patients.
Figure 5A:
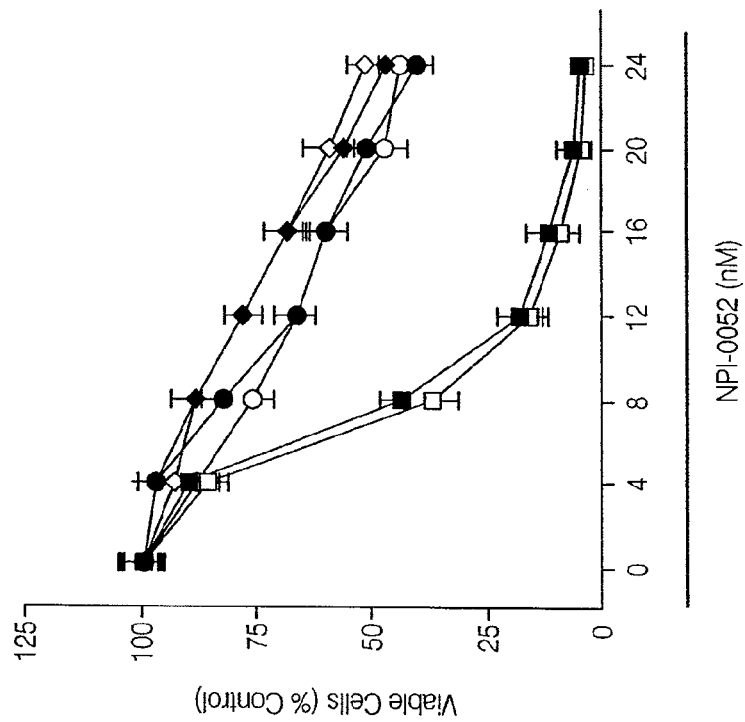
FIG. 5A illustrates cell viability of various multiple myeloma cell lines treated with indicated doses of NPI-0052 for 24 h.

Cell viability was assessed by 3-(4,5-dimethylthiazol-2-yl)-2,5-diphenyltetrazolium bromide (MTT; Chemicon International Inc., Temecula, Calif.) assay, according to manufacturer's instructions (Roche Molecular Biochemicals, Indianapolis, Ind.), and as described in Chauhan, D., Catley, L., Hideshima, T., Li, G., Leblanc, R., Gupta, D., Sattler, M., Richardson, P., Schlossman, R. L., Podar, K., Weller, E., Munshi, N. & Anderson, K. C. (2002) Blood 100, 2187-94; which is incorporated herein by reference in its entirety. Cell viability after treatment of MM.1S (-■-), Dex-resistant MM.1R (-□-), RPMI-8226 (-●-), Doxorubicin-resistant Dox-40 (-◆-), OPM2 (-○-), and U266 (-◇-) cells with the compound of formula (II) (X=Cl) for 24 h is illustrated in FIG. 5A. Results are mean±S.D from three independent experiments (P<0.005; n=3 for all cell lines). A dose-dependent significant decrease in cell viability in all cell lines was observed (IC$_{50}$ range 7-24 nM).

Cell viability was also assessed on purified patient MM cells. Freshly isolated tumor cells from nine MM patients relapsing after multiple prior therapies including Dex, Bortezomib, and thalidomide were treated with the compound of formula (II) (X=Cl) (10 nM) for 24 h and analyzed for apoptosis. As seen in FIG. 5B, significant apoptosis was observed in these cells as measured by DNA fragmentation assays (P<0.005; n=2). Plotted values are the mean±SD of triplicate samples. Importantly, 4 of 9 patients examined were refractory to Bortezomib therapy, and 5 patients were resistant to Thalidomide and Dex therapies. These data suggest that 1) the compound of formula (II) (X=Cl) induces apoptosis in MM cells sensitive and resistant to conventional and Bortezomib therapies; and 2) IC$_{50}$ of the compound for MM cells is within the nanomolar concentration.

Example 7

Effect on Bone Marrow Stromal Cell (BMSCs) Viability

Figures 6, 7:
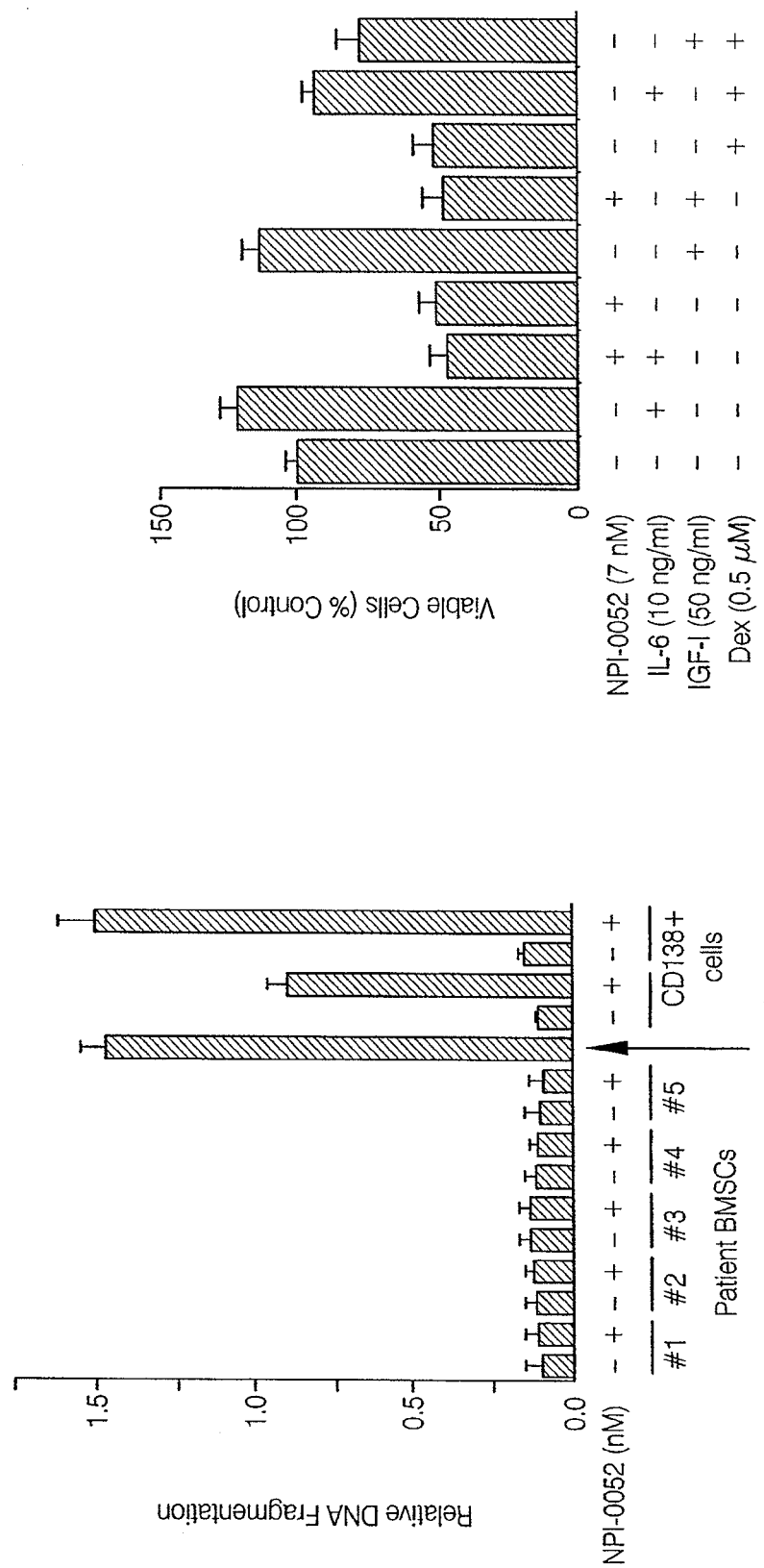
FIG. 6 illustrates DNA fragmentation assays of apoptosis after treatment with NPI-0052 of bone marrow stromal cells obtained from patients.
FIG. 7 illustrates MTT assay of MM.1S cell viability after treatment with NPI-0052 or Dex in the presence or absence of IL-6 or IGF-I.

MM cells predominantly localize in the bone marrow microenvironment and their interaction with BMSCs induces production of cytokines which mediate growth of MM cells, as well as protect against drug-induced apoptosis. See Anderson, K. C. (2003) Cancer 97, 796-801; which is incorporated herein by reference in its entirety. Therefore, the effect of the compound of formula (II) (X=Cl) on five patient MM-derived BMSCs was determined. As seen in FIG. 6, treatment of BMSCs (Patient#1-5) with the compound of formula (II) (X=Cl) (20 nM) for 24 h does not induce apoptosis in these cells, as evidenced by DNA fragmentation assay. Positive control shown is an internal control for the assay. Purified MM cells (CD138+) from two of the five MM patient were also examined within the same experiments. Results are mean±SD from triplicate samples. The compound triggered a significant (10-12 fold) increase in apoptosis of purified (CD138-positive) patient MM cells. These results suggest that the compound of formula (II) (X=Cl) acts directly on MM cells, but not BMSCs.

Example 8

Effect of Recombinant Human Interleukin-6 (rhIL-6) and Recombinant Human Insulin-Like Growth Factor-I (rhIGF-I) Anti-Apoptotics Adhesion of MM cells to BMSCs induces IL-6 and IGF-I secretion from BMSCs, which not only regulates the growth of MM cells, but also protects against chemotherapy. See Hardin, J., MacLeod, S., Grigorieva, I., Chang, R., Barlogie, B., Xiao, H. & Epstein, J. (1994) Blood 84, 3063-70 and Chauhan, D., Kharbanda, S., Ogata, A., Urashima, M., Teoh, G., Robertson, M., Kufe, D. W. & Anderson, K. C. (1997) Blood 89, 227-234; both of which are incorporated herein by reference in their entirety. Thus, whether rhIL-6 or rhIGF-I inhibits apoptosis in MM cells induced by the compound of Formula (II) (X=Cl) was evaluated. MM.1S cells were treated with the compound of formula (II) (X=Cl) (7 nM) or Dex (0.5 µM) for 24 h, in the presence and absence of rhIL-6 (10 ng/ml) or rhIGF (50 ng/ml). At 24 h cells were harvested and viability analyzed by MTT assays. As seen in FIG. 7, the median cell viability was 47±2.3% after treatment with the compound alone; 51.2±3.2% with the compound+rhIL-6 (P=0.26, Wilcoxon test), and 50.3%±2.0% with the compound+rhIGF-I (P=0.28). Median viability was 51±2.1% after treatment with Dex and 92±5.5% for Dex+rhIL-6 (P=0.05, as determined by one-sided Wilcoxon rank-sum test). Results are mean±SD of three independent experiments. These findings suggest that neither IL-6 nor IGF-I block the anti-MM activity of the compound of formula (II) (X=Cl). In contrast and as in other studies, both IL-6 and IGF-I block Dex-induced decreased MM.1S cell viability. See Chauhan, D., Hideshima, T. & Anderson, K. C. (2003) Int J Hematol 78, 114-20 and Mitsiades, C. S., Mitsiades, N., Poulaki, V., Schlossman, R., Akiyama, M., Chauhan, D., Hideshima, T., Treon, S. P., Munshi, N. C., Richardson, P. G. & Anderson, K. C. (2002) Oncogene 21, 5673-83; both of which are incorporated herein by reference in their entirety. Thus, the data suggests that the compound of formula (II) (X=Cl) overcomes the growth and protective effects of IL-6 and IGF-I on MM cells, and indicate distinct mechanisms of action for the compound and Dex against MM cells. Reports that high serum levels of IL-6 contribute to clinical chemoresistance and treatment failure, coupled with the ability of the compound of formula (II) (X=Cl) to induce MM cell apoptosis even in the presence of IL-6 or IGF-I, suggest that the compound may overcome drug resistance in patients with advanced MM. See Kyrstsonis, M. C., Dedoussis, G., Baxevanis, C., Stamatelou, M. & Maniatis, A. (1996) Br J Haematol 92, 420-422; which is incorporated herein by reference in its entirety.

Example 9

Figures 8, 9:
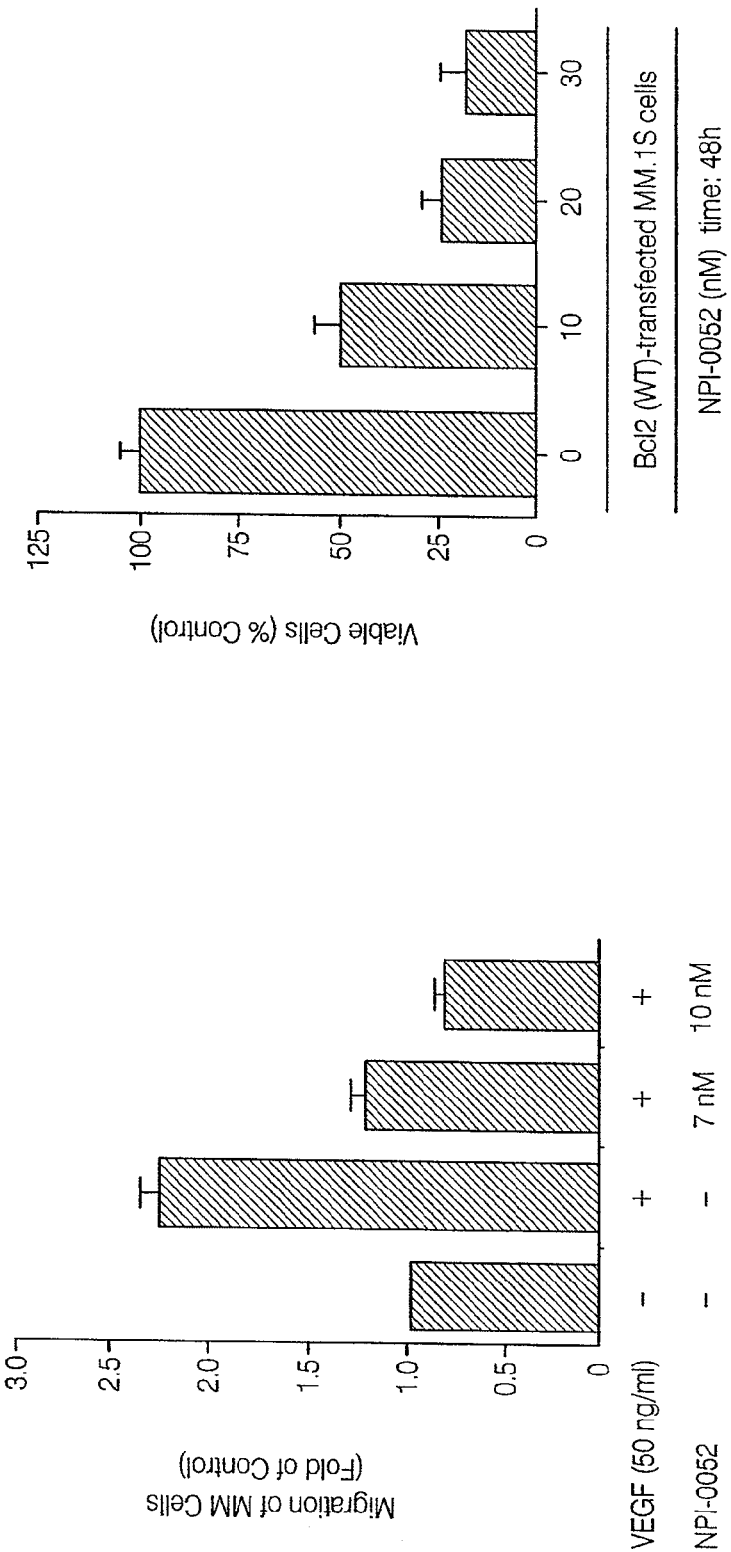
FIG. 8 illustrates the effect of NPI-0052 on VEGF-induced migration of MM.1S cells.
FIG. 9 illustrates the effect of NPI-0052 on Bcl2-overexpressing MM.1S cell viability.

Effect on Vascular Endothelial Growth Factor (VEGF) Induced Migration of MM Cells VEGF is elevated in the bone marrow microenvironment and triggers migration, growth, and angiogenesis in MM cells. See Podar, K., Tai, Y. T., Lin, B. K., Narsimhan, R. P., Sattler, M., Kijima, T., Salgia, R., Gupta, D., Chauhan, D. & Anderson, K. C. (2002) J Biol Chem 277, 7875-81; which is incorporated herein by reference in its entirety. Thus, whether the compound of formula (II) (X=Cl) alters VEGF-induced migration of MM cells was evaluated. VEGF induced migration was examined in the presence or absence of the compound (7 or 10 nM). Cell migration was assayed as described previously in Podar, K., Tai, Y. T., Davies, F. E., Lentzsch, S., Sattler, M., Hideshima, T., Lin, B. K., Gupta, D., Shima, Y., Chauhan, D., Mitsiades, C., Raje, N., Richardson, P. & Anderson, K. C. (2001) Blood 98, 428-35; which is incorporated herein by reference in its entirety. As shown in FIG. 8, the compound of formula (II) (X=Cl) significantly (P<0.05) decreases VEGF-induced migration of MM.1S MM cells. These findings indicate that the compound may negatively regulate both homing of MM cells to the bone marrow and their egress into the peripheral blood.

Example 10

Effect on Bcl2-Mediated Protective Effects

Bcl2 confers resistance to conventional therapies in cancer cells, including MM. See Cory, S. & Adams, J. M. (2002) Nat Rev Cancer 2, 647-56 and Gazitt, Y., Fey, V., Thomas, C. & Alvarez, R. (1998) Int J Oncol 13, 397-405; both of which are incorporated herein by reference in their entirety. Bcl2 can modestly attenuate Bortezomib-induced apoptosis. Thus, whether ectopic expression of Bcl2 in MM.1S cells affects responsiveness to the compound of formula (II) (X=Cl) was evaluated. MM.1S cells were stably transfected with Bcl2 construct and analyzed for alterations in cell viability using an MTT assay. As seen in FIG. 9, the compound of formula (II) (X=Cl) significantly decreases cell viability of Bcl2-transfected MM.1S cells (P<0.005) in a dose-dependent manner. Nonetheless, the compound induced 15±1.1% less cell death in Bcl2-transfected cells compared to empty vector-transfected MM.1S cells. Results are mean±SD of three independent experiments. These findings suggest that the compound can overcome Bcl2-mediated protection.

Example 11

In Vivo Evaluation in Murine Tumor Model

Six-week-old triple immune deficient beige-nude-xid (BNX) mice were obtained from Frederick Cancer Research and Development Center (Frederick, Md.). All animal studies were conducted according to protocols approved by the Animal Ethics Committee of the Dana-Farber Cancer Institute. Mice were observed daily for signs of toxicity. Terminal bleeding was done under anesthesia using isoflourane inhalation, and animals were sacrificed by $CO_2$ asphyxiation. To determine the in vivo anti-MM activity of the compound of formula (II) (X=Cl), 21 BNX mice were inoculated subcutaneously in the flank with $3 \times 10^7$ RPMI 8226 MM cells in 100 µl of RPMI-1640 media. When tumors became measurable, mice were assigned to treatment groups receiving the compound of formula (II) (X=Cl) 0.25 mg/kg (n=7), 0.5 mg/kg (n=7), or to control groups (n=7) receiving the vehicle only. Drug treatment was started after the development of measurable tumor. The drug (0.25 mg/kg or 0.5 mg/kg) was given orally twice a week. Serial caliper measurements of perpendicular diameters were done every other day to calculate tumor volume, using the following formula: 4/24×(shortest diameter)2×(longest diameter). Animals were sacrificed if the tumor was ≥2 cm or necrotic. For tumor growth studies, 7 mice were used in each group.

Figure 10A:
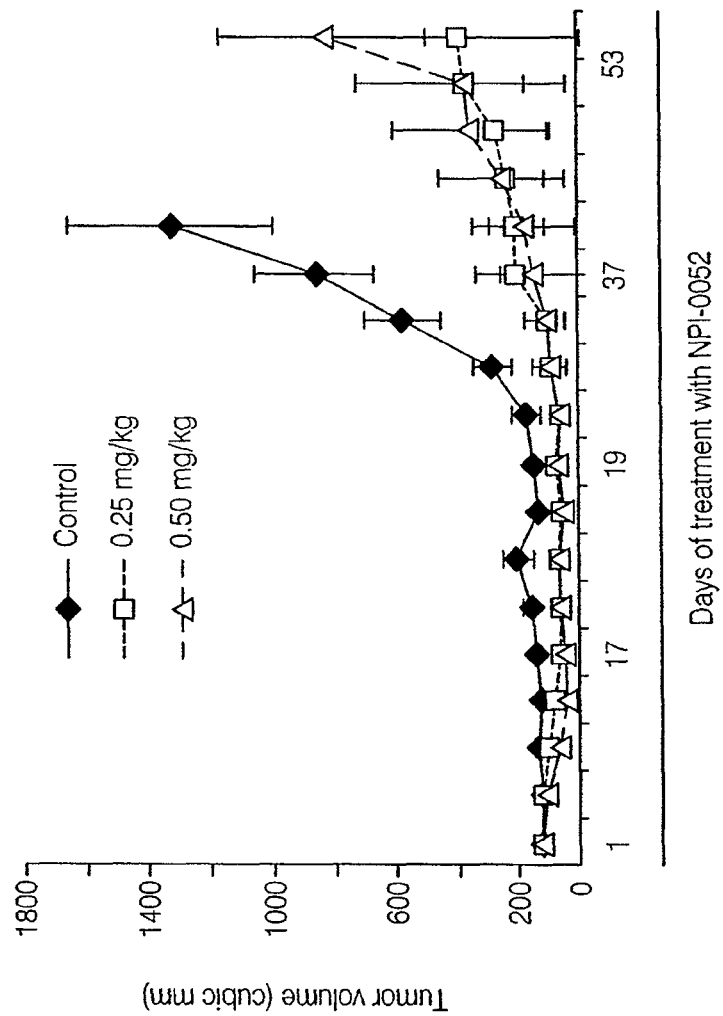
FIGS. 10A and 10B depict the effect of NPI-0052 on tumor growth when administered orally to mice.
Figure 10B:
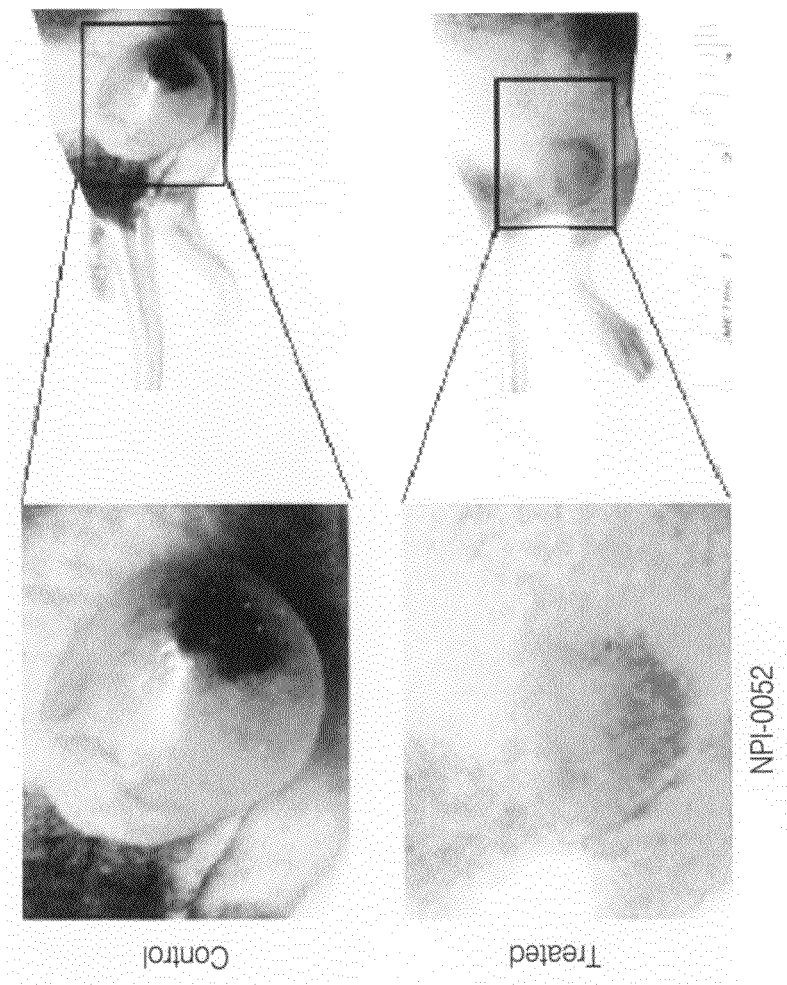
Figure 10C:
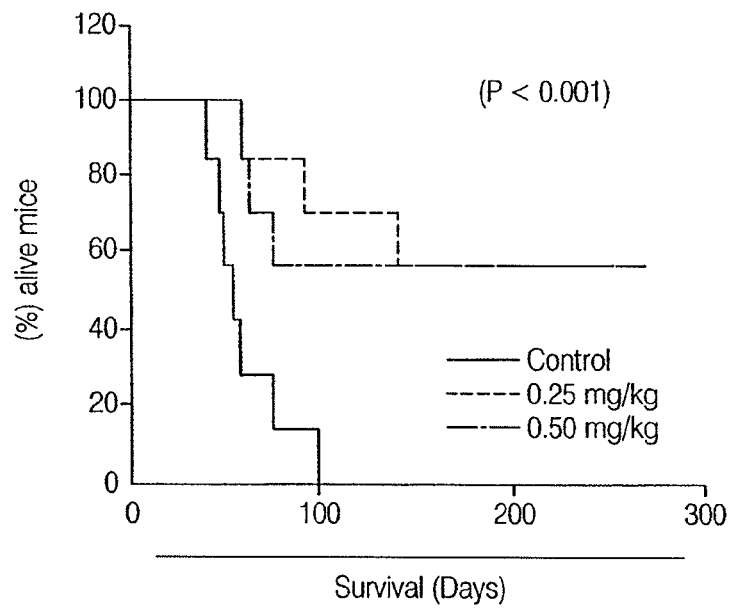
FIG. 10C illustrates the effect of NPI-0052 on survival when administered orally to mice.
Figure 10D:
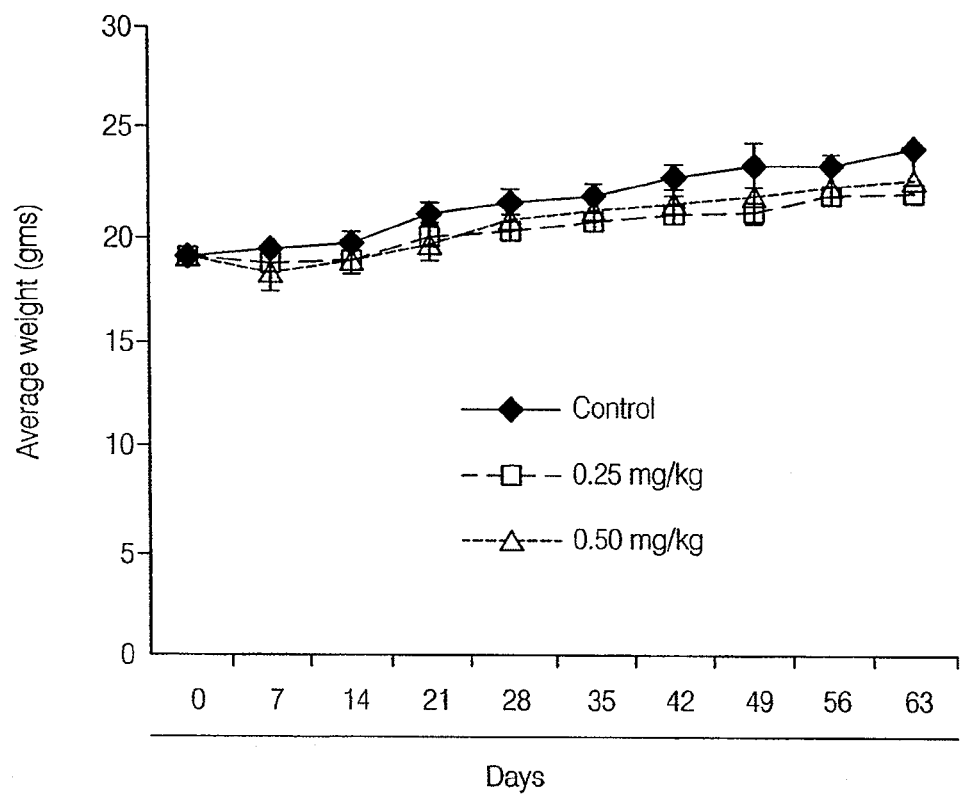
FIG. 10D illustrates the effect of NPI-0052 on body weight when administered orally to mice.

As seen in FIGS. 10A-C, treatment of tumor bearing mice with the compound of formula (II) (X=Cl), but not with vehicle alone, significantly inhibits MM tumor growth and prolongs survival of these mice. All mice in the control group developed progressive tumors, whereas complete regression of tumors were observed in 70% of treated mice. The mouse on the upper panel of FIG. 10B received oral doses of vehicle alone, whereas the mouse on the lower panel received the compound of formula (II) (X=Cl) (0.25 mg/kg). The left panels in FIG. 10B are enlargements of subcutaneous plasmacytomas growing on the right flanks of the mice. Survival was evaluated from the first day of treatment until death; mice were sacrificed when their tumor diameters reached 2 cm or they became moribund (FIG. 10C). Moreover, no neurological behavioral changes were observed even after 12 weeks of treatment. The concentrations of the compound administered were well tolerated by mice, without evidence of weight loss. Mice in both untreated and treated group were weighed every week. The average changes in the mice body weight are shown in FIG. 10D.

Figure 10E:
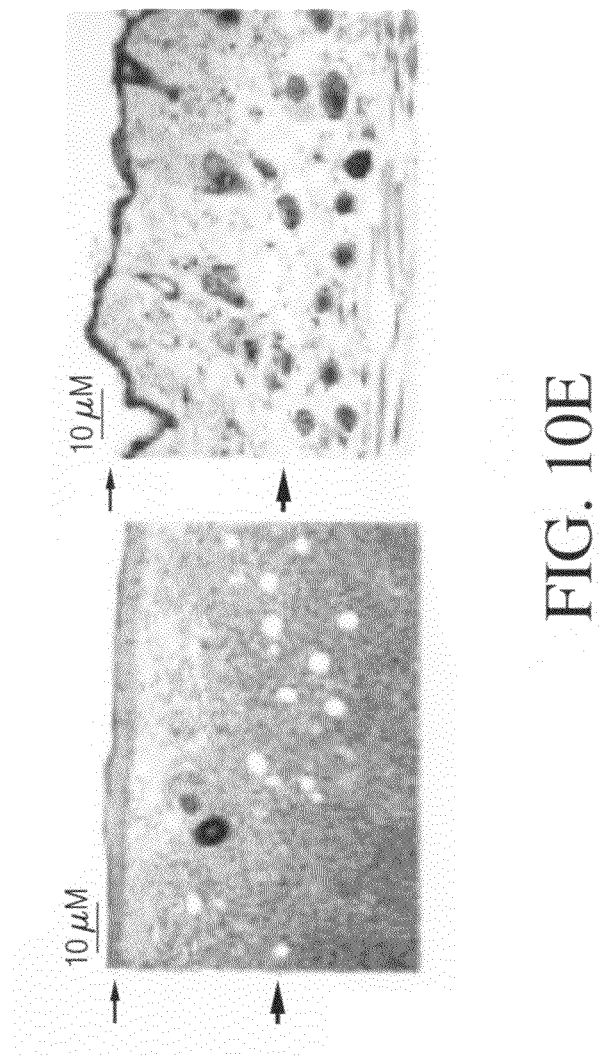
FIG. 10E illustrates tissue sections of inoculation sites from NPI-0052-treated and control-treated mice.

Analysis at day 300 showed no recurrence of tumor in 57% of the compound of formula (II) (X=Cl)-treated mice (FIG. 10C). In addition, histologic analysis performed on the inoculation sites confirmed the disappearance of plasma cells in the compound of formula (II) (X=Cl)—versus vehicle-treated mice (FIG. 10E, left and right panels, respectively). These data show that the compound is orally active; inhibits MM tumor growth in vivo; and prolongs survival.

Example 12

Comparative Analysis of In Vivo Antitumor Activity

Figure 10F:
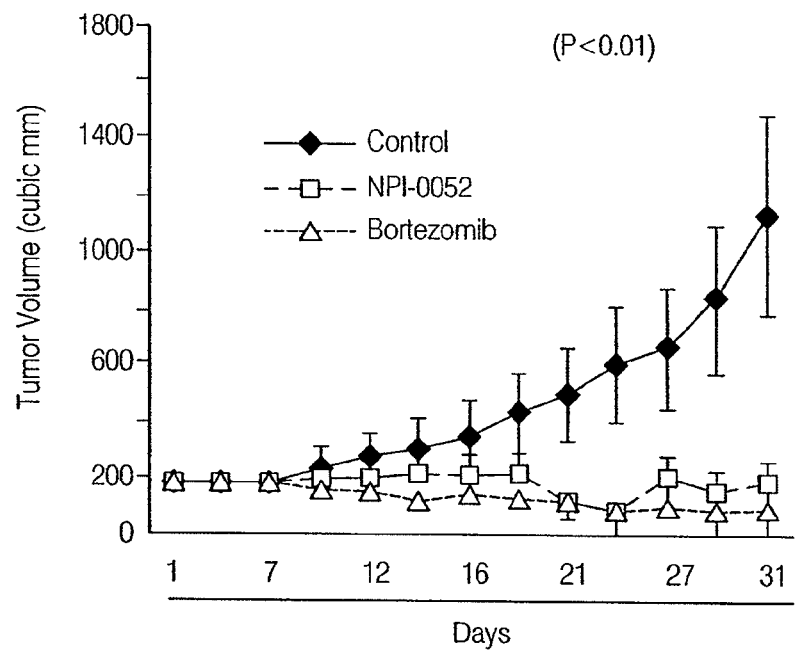
FIG. 10F compares the effect of NPI-0052 and Bortezomib on tumor growth when administered i.v. to mice.
Figure 10G:
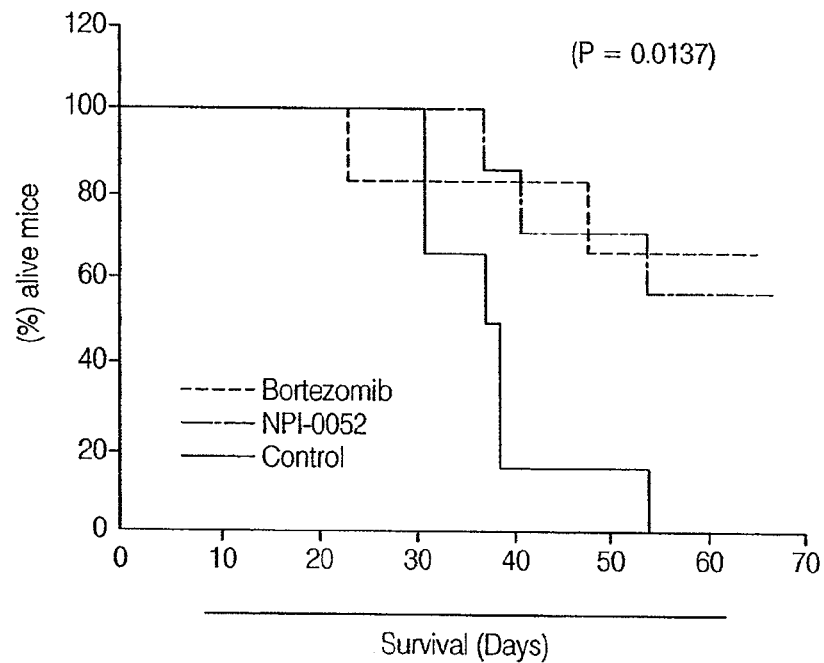
FIG. 10G compares the effect of NPI-0052 and Bortezomib on survival when administered i.v. to mice.

To compare the in vivo activity of the compound of formula (II) and Bortezomib, the mice models as described above were treated with the compound of formula (II) (X=Cl) (0.15 mg/kg i.v.) or Bortezomib (1.0 mg/kg i.v.) twice weekly. Both agents significantly reduced the tumor progression (p<0.01) and prolonged survival (p=0.0137) (FIGS. 10F and 10G).

Example 13

Mechanisms Mediating Anti-MM Activity

Mitochondria play a critical role in apoptosis induction during stress. See Bossy-Wetzel, E. & Green, D. R. (1999) *Mutat Res* 434, 243-51 and Chauhan, D. & Anderson, K. C. (2003) *Apoptosis* 8, 337-43; both of which are incorporated herein by reference in their entirety. Serum starved MM.1S cells were treated with the compound of formula (II) (X=Cl) (7 nM) for 12 h and incubated with CMXRos for the last 20 min; stained with lipophilic cationic dye CMXRos (Mitotracker Red) (Molecular Probes, Eugene, Oreg.) in phosphate-buffered saline (PBS) for 20 mins at 37° C.; and analyzed by flow cytometry to assay for alterations in ? Ψm (mitochondrial membrane potential). Superoxide ($O_2$) production was measured by staining cells with membrane permeable dye dihydroethidium (HE) for the last 15 min. Superoxide anions oxidize HE to fluorescent ethidium, permitting analysis by flow cytometry.

Figure 11B:
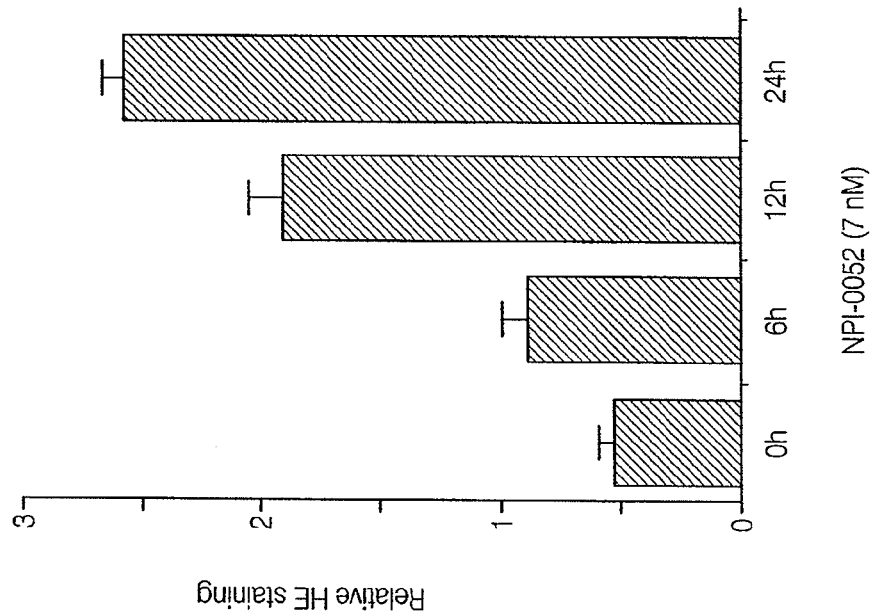
FIG. 11B illustrates the effect of NPI-0052 on superoxide generation in MM.1S cells stained with membrane permeable dye dihydroethidium (HE).
Figure 11A:
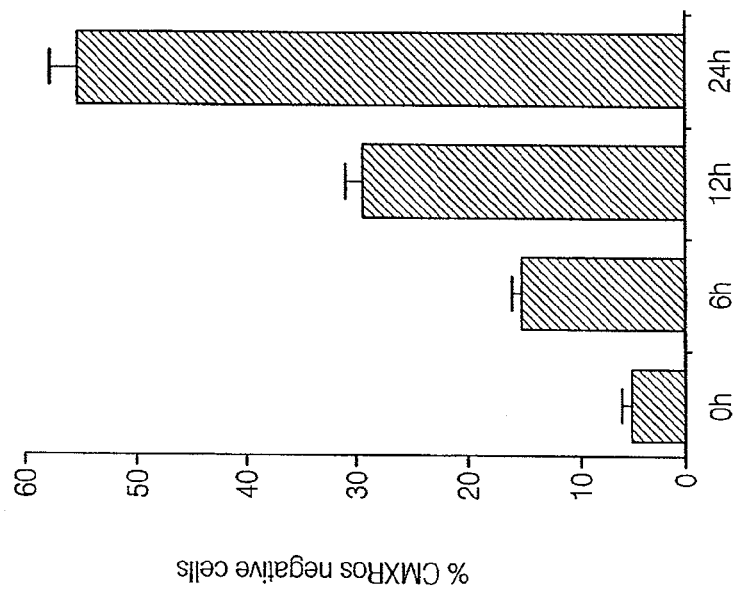
FIG. 11A illustrates the effect of NPI-0052 on mitochondrial membrane potential in MM.1S cells incubated with CMXRos.

As seen in FIGS. 11A and 11B, the compound of formula (II) (X=Cl) decreases ΔΨm, evidenced by an increased number of CMXRos negative cells (P<0.005, n=2), and triggers $O_2$ production in MM.1S cells. Results are mean±SD of two independent experiments. Alterations in ΔΨm are associated with release of mitochondrial proteins cyto-c and Smac to the cytosol, thereby triggering caspase 9 and caspase-3. See Du, C., Fang, M., Li, Y., Li, L. & Wang, X. (2000) *Cell* 102, 33-42 and Liu, X., Naekyung Kim, C., Yang, J., Jemmerson, R. & Wang, X. (1996) *Cell* 86, 147-157; both of which are incorporated herein by reference in their entirety.

Figure 11C:
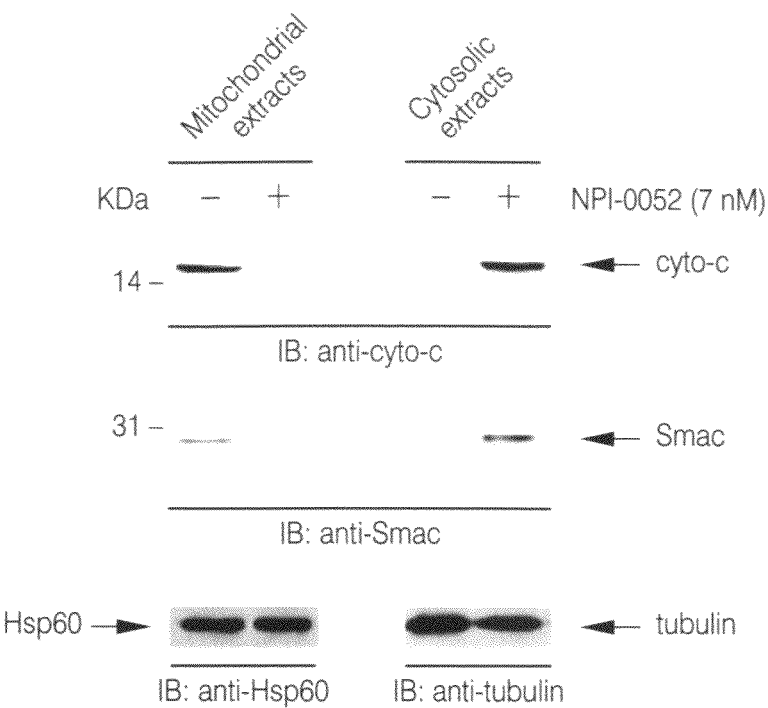
FIG. 11C depicts immunoblots of mitochondrial and cytosolic protein fractions obtained from MM.1S cells treated with NPI-0052.

As seen in FIG. 11C, treatment of MM.1S cells with compound of formula (II) (X=Cl) triggers a decrease in mitochondrial cyto-c (upper, left panel) and smac (upper, right panel), and a concurrent increase of these proteins in the cytosolic fractions (middle, left and right panels, respectively). Reprobing the immunoblots with anti-Hsp60 (lower, left panel) and anti-tubulin (lower, right panel) Abs confirms purity of mitochondrial extracts and equal protein loading. Release of mitochondrial apoptogenic proteins cyto-c and Smac/DIABLO induce activation of caspases-9 and -3. MM.1S cells were treated with the compound of formula (II) (X=Cl) (7 nM) for 24 h and harvested; mitochondrial and cytosolic protein fractions were separated by 12.5% SDS-PAGE and analyzed by immunoblotting with anti-cyto-c (upper panel) or anti-Smac (middle panel) Abs. As a control for equal loading of proteins and purity of mitochondrial fractions, filters were also reprobed with anti-tubulin (lower right panel) and anti-Hsp60 Abs (lower left panel), respectively. Blots are representative of three independent experiments.

Figure 11D:
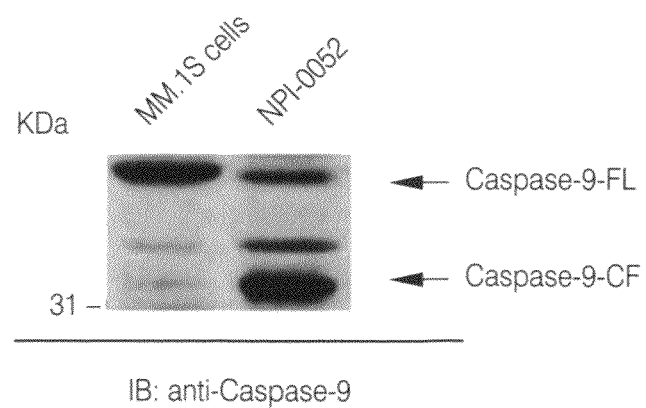
FIG. 11D depicts immunoblots of cytosolic proteins obtained from MM.1S cells treated with NPI-0052 and analyzed with anti-caspase-9 Abs.
Figure 11E:
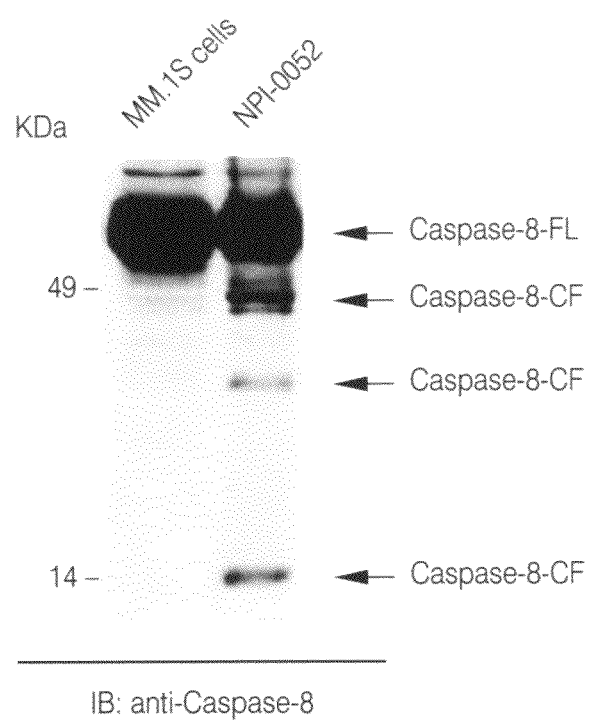
FIG. 11E depicts immunoblots of cytosolic proteins obtained from MM.1S cells treated with NPI-0052 and analyzed with anti-caspase-8 Abs.
Figure 11F:
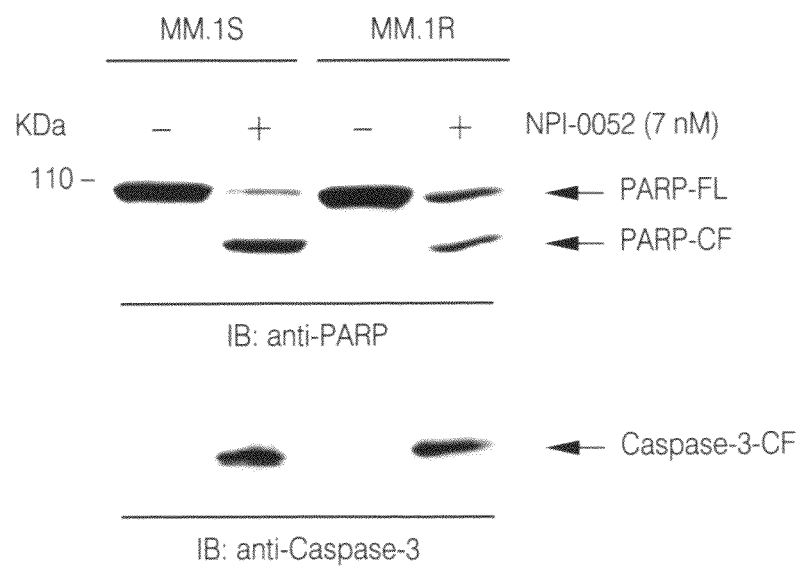
FIG. 11F depicts immunoblots of MM.1S or MM.1R MM cells treated with NPI-0052 and assessed for apoptosis by both PARP and caspase-3 cleavage assays.

MM.1S cells were treated with the compound of formula (II) (X=Cl) (7 nM) for 24 h and harvested; cytosolic proteins were separated by 12.5% SDS-PAGE and analyzed by immunoblotting with anti-caspase-8 Abs and anti-caspase-9 Abs. As seen in FIG. 11D, treatment of MM.1 S cells with the compound of formula (II) (X=Cl) induces proteolytic cleavage of caspase-9. Moreover, the compound also activates caspase-8 (FIG. 11E). Both caspase-9 (mitochondria-dependent) and caspase-8 (mitochondria-independent) are known to proteolytically cleave and activate a common downstream effector caspase-3, resulting in PARP cleavage. See Miller, L. K. (1999) *Trends Cell Biol* 9, 323-8; which is incorporated herein by reference in its entirety. Thus, MM.1S or MM.1R MM cells were treated with the compound of formula (II) (X=Cl) (7 nM) for 24 h and assessed for apoptosis by both PARP and caspase-3 cleavage assays. Total protein lysates were subjected to SDS-PAGE analysis. Immunoblot analysis of the lysates was performed with anti-PARP (upper panel) or anti-caspase-3 (lower panel) Abs. 'FL' indicates 'full length' and 'CF' denotes cleaved fragment. This data further shows that the compound of formula (II) (X=Cl) triggers caspase-3 and PARP cleavage (FIG. 11F).

Immunoblot analysis was performed using antibodies to cytochrome-c, Smac, Caspase-8, -9, or -3 (Cell Signaling, Beverly, Mass.), tubulin (Sigma, St. Louis, Mo.), PARP, Hsp60, or Bax (BD Bioscience Pharmingen, San Diego, Calif.). Blots were developed by enhanced chemiluminescence (ECL; Amersham, Arlington Heights, Ill.).

Example 14

Mechanistic Differences of MM Cell Apoptosis Compared to Bortezomib

Figure 12B:
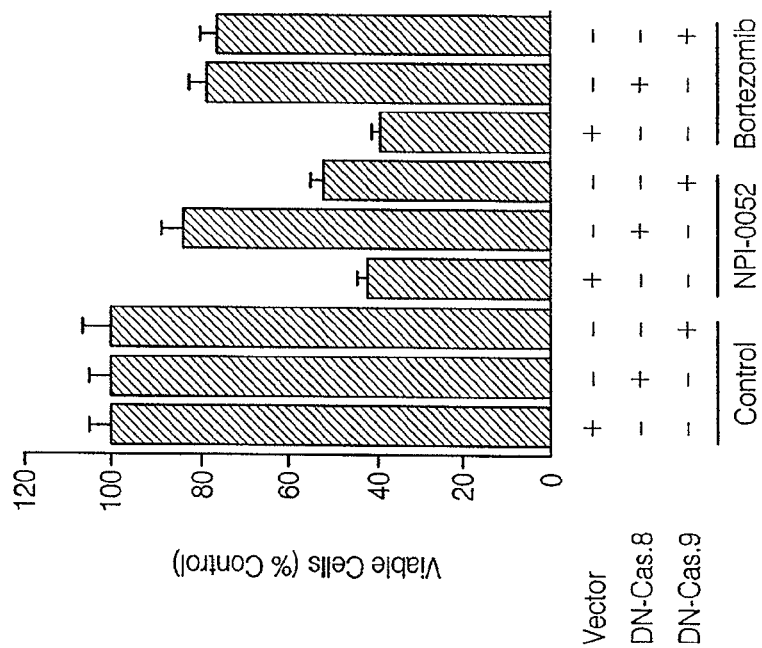
FIG. 12B illustrates MM.1S cell viability for cells transfected with vector alone, DN-caspase-8, and DN-caspase-9 after treatment with NPI-0052 or Bortezomib.
Figure 12A:
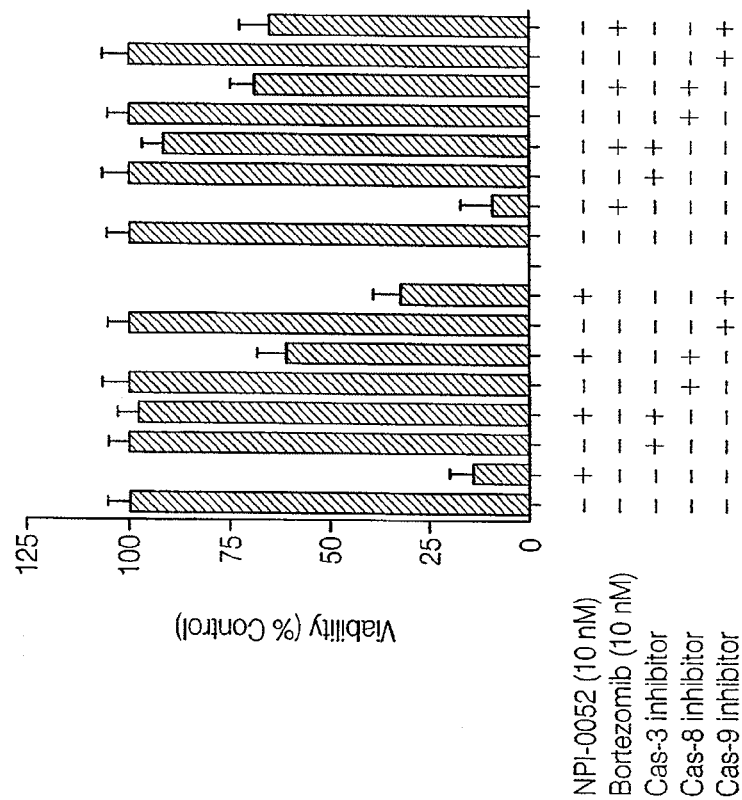
FIG. 12A illustrates MM.1S cell viability after treatment with NPI-0052 or Bortezomib in the presence or absence of caspase-3, caspase-8, or caspase-9 inhibitor.

MM.1S cells were treated with the compound of formula (II) (X=Cl) or Bortezomib in the presence or absence of caspase-9 inhibitor (LEHD-FMK), caspase-8 inhibitor (IETD-fmk) or caspase-3 inhibitor (Z-Val-Ala-Asp-fluoromethylketone, z-VAD-fmk). As seen in FIG. 12A, caspase-3 inhibition markedly abrogates both the compound of formula (II) (X=Cl) and Bortezomib-induced apoptosis. Results are mean±SD of four independent experiments (P<0.004).

Blockade of caspase-8 led to a significant decrease in cell death triggered by the compound of formula (II) (X=Cl) (P<0.005, n=4), whereas inhibition of caspase-9 only moderately blocked decreased viability in MM.1S cells triggered by the compound. In contrast, Bortezomib-induced decrease in viability of MM.1S cells is equally blocked in the presence of either caspase-8 or caspase-9 inhibitor (P<0.005). Together, these data suggest that caspase-8 and caspase-9 activation equally contribute during Bortezomib-triggered cell death, whereas apoptosis triggered by the compound of formula (II) (X=Cl) proceeds primarily via caspase-8 signaling pathway.

Figure 12C:
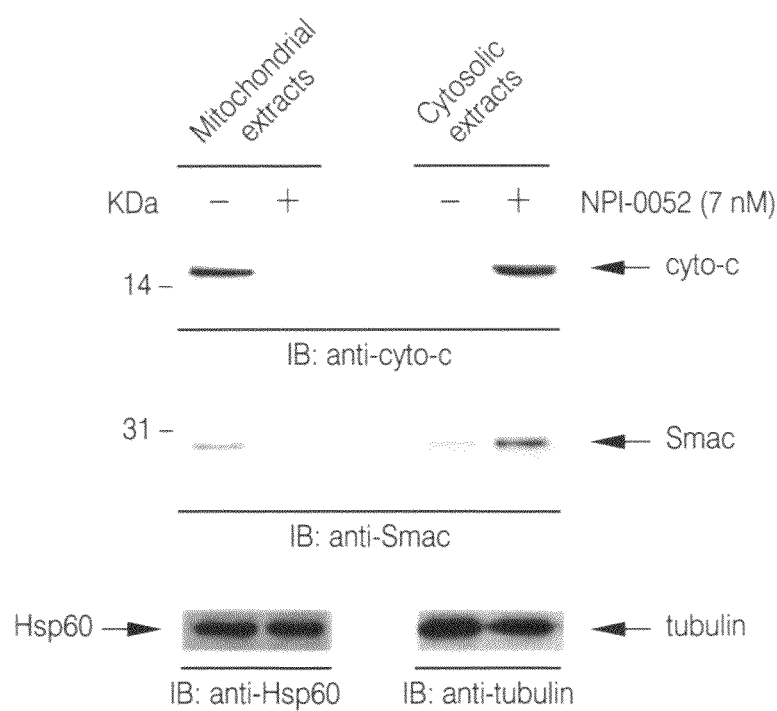
FIG. 12C depicts immunoblots of cytosolic extracts from DN-caspase-8 and DN-caspase-9 transfected MM.1S cells treated with dexamethasone or anti-Fas MoAb.

These biochemical data were confirmed by genetic studies using dominant-negative (DN) strategies. MM.1S cells were also transiently transfected using Cell line Nucleofecto kit V, according to the manufacturer's instructions (Amaxa Biosystems, Germany), with vector alone, DN-caspase-8, DN-caspase-9, or DN-FADD and cotransfected with vector containing green fluorescence protein (GFP) alone. Following transfections, GFP-positive cells were selected by flow cytometry, treated with the compound of formula (II) (X=Cl) or Bortezomib, and analyzed for viability. Treatment of DN-caspase-8-transfected MM cells with the compound of formula (II) (X=Cl) (IC50, 7 nM) markedly increased survival of these cells, compared to the cells transfected with DN-caspase-9 (FIG. 12B). In contrast, treatment of either DN-caspase-8 or DN-caspase-9-transfected MM.1S cells with Bortezomib (IC50, 5 nM) increased the survival to a similar extent. The functional specificity of DNcaspase-8 and DN-caspase-9 was confirmed by treatment of MM.1S cells with known inducers of caspase-9 (Dex) and caspase-8 in these cells (anti-Fas MoAb) (Chauhan et al., 1997) (FIG. 12C). These data suggest that (1) compound of formula (II) (X=Cl)-induced MM cell apoptosis is predominantly mediated by caspase-8; and (2) Bortezomib-induced apoptosis requires both caspase-8 and caspase-9 activation.

Figure 12D:
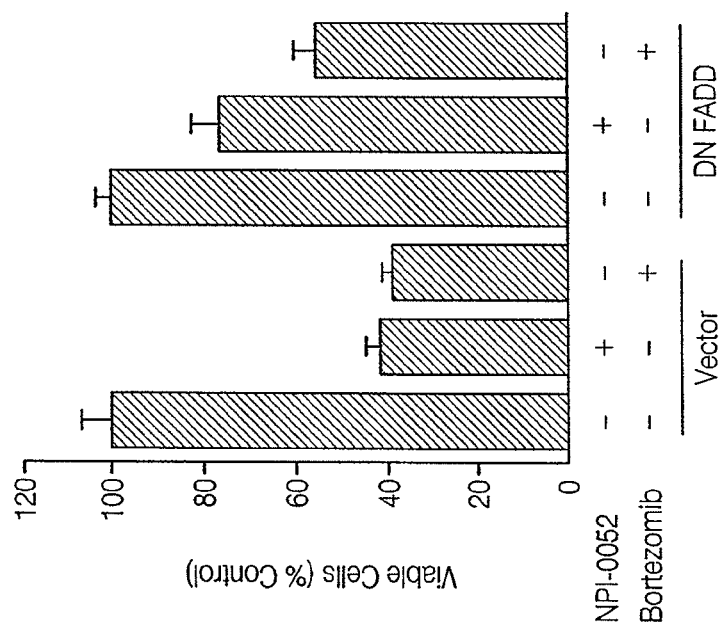
FIG. 12D illustrates MM.1S cell viability for vector or DN-FADD transfected cells after treatment with NPI-0052 or Bortezomib.

It was next determined whether inhibition of an upstream signaling pathway that leads to caspase-8 activation affects the response to the compound of formula (II) (X=Cl) or Bortezomib. The Fas-associated death domain (FADD) protein is an important part of the deathinducing signaling complexes (DISCs) that assemble upon engagement of TNF receptor family members, such as Fas, resulting in proteolytic processing and autoactivation of pro-caspase-8. Since both the compound of formula (II) (X=Cl) and Bortezomib trigger caspase-8 activation, the role of FADD during this event in MM cells was evaluated using DN-FADD. Blockade of FADD with DN-FADD significantly attenuated compound of formula (II) (X=Cl)-induced cytotoxicity compared to the empty vector-transfected MM.1S cells (42%±2.0% viable cells in vector-transfected cells versus 76%±5.1% viable cells in DN-FADD-transfected cells; p<0.05) (FIG. 12D). DN-FADD decreased compound of formula (II) (X=Cl)-induced caspase-8 activation; however, minimal caspase-8 activation was still noted (data not shown), which may be due to upstream activators of caspase-8 other than FADD. Importantly, treatment of DN-FADD-transfected MM.1S cells with Bortezomib resulted in only a 16% increase in survival compared to vector-transfected cells (39%±2.4% viable cells in vector-transfected cells versus 55%±4.1% viable cells in DN-FADD-transfected cells; p<0.05) (FIG. 12D). These data, coupled with caspase-8 or caspase-9 inhibition studies, suggest that the compound of formula (II) relies more on FADD-caspase-8 signaling axis than does Bortezomib, further confirming differential mechanism of action of the compound of formula (II) versus Bortezomib in MM cells.

Figure 12E:
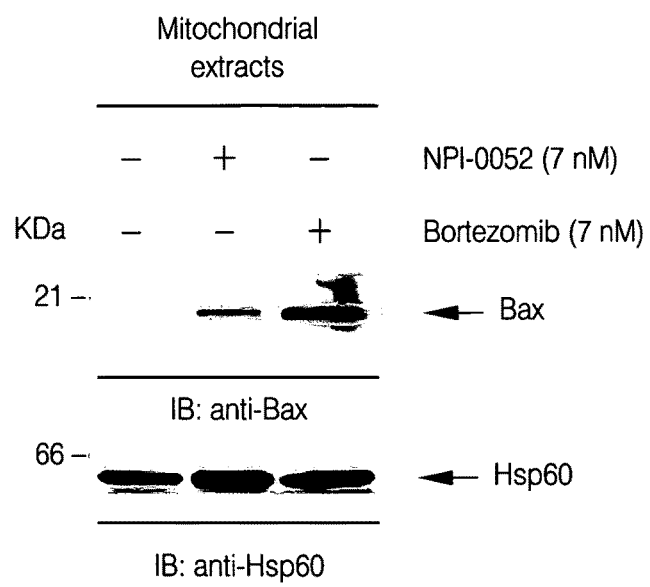
FIG. 12E depicts immunoblots of mitochondrial protein extracts from MM.1S MM cells treated with indicated concentration of either NPI-0052 or Bortezomib and analysed with anti-Bax or anti-Hsp60 Abs.

Previous studies have established that Bax induces mitochondrial apoptotic pathway. See Wei, M. C., Zong, W. X., Cheng, E. H., Lindsten, T., Panoutsakopoulou, V., Ross, A. J., Roth, K. A., MacGregor, G. R., Thompson, C. B. & Korsmeyer, S. J. (2001) Science 292, 727-30 and Lei, K., Nimnual, A., Zong, W. X., Kennedy, N. J., Flavell, R. A., Thompson, C. B., Bar-Sagi, D. & Davis, R. J. (2002) Mol Cell Biol 22, 4929-42; both of which are incorporated herein by reference in their entirety. Thus, whether MM cell apoptosis induced by the compound of formula (II) (X=Cl) correlates with alterations in Bax was evaluated. MM.1S MM cells were treated with either the compound of formula (II) (X=Cl) or Bortezomib and mitochondrial protein extracts were subjected to immunoblot analysis with anti-Bax or anti-Hsp60 Abs. As seen in FIG. 12E, the compound of formula (II) (X=Cl) induces little, if any increase in Bax levels in mitochondria. Blots are representatives of three independent experiments. Importantly, Bortezomib triggers a significant accumulation of Bax in mitochondria.

Figure 12F:
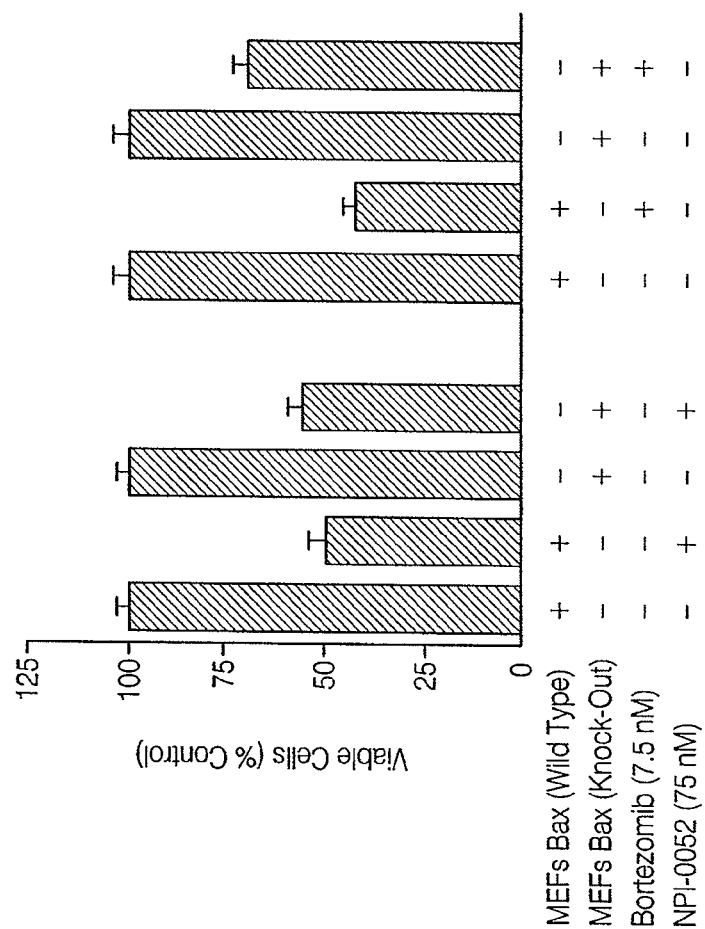
FIG. 12F illustrates cell viability of mouse embryonic fibroblasts (MEFs) cells with either wild-type or deleted Bax (knock-out) treated with indicated concentrations of NPI-0052 or Bortezomib.

Mouse embryonic fibroblast (MEFs) carrying wild-type Bax or knock-outs were treated with the compound of formula (II) (X=Cl) or Bortezomib for 48 h and analyzed for cell viability by MTT assays. As seen in FIG. 12F, the compound of formula (II) (X=Cl) decreases viability in both Bax (WT) and Bax (knock-out), whereas deletion of Bax confers significant resistance to Bortezomib. Results are mean±SD of three independent experiments (P<0.05). These data show the differential requirement of Bax during apoptosis induced by the compound of formula (II) (X=Cl) and Bortezomib and suggest distinct mechanism of action of these agents.

Example 15

Differential Effects on Normal Lymphocytes as Compared to Bortezomib

Figure 13:
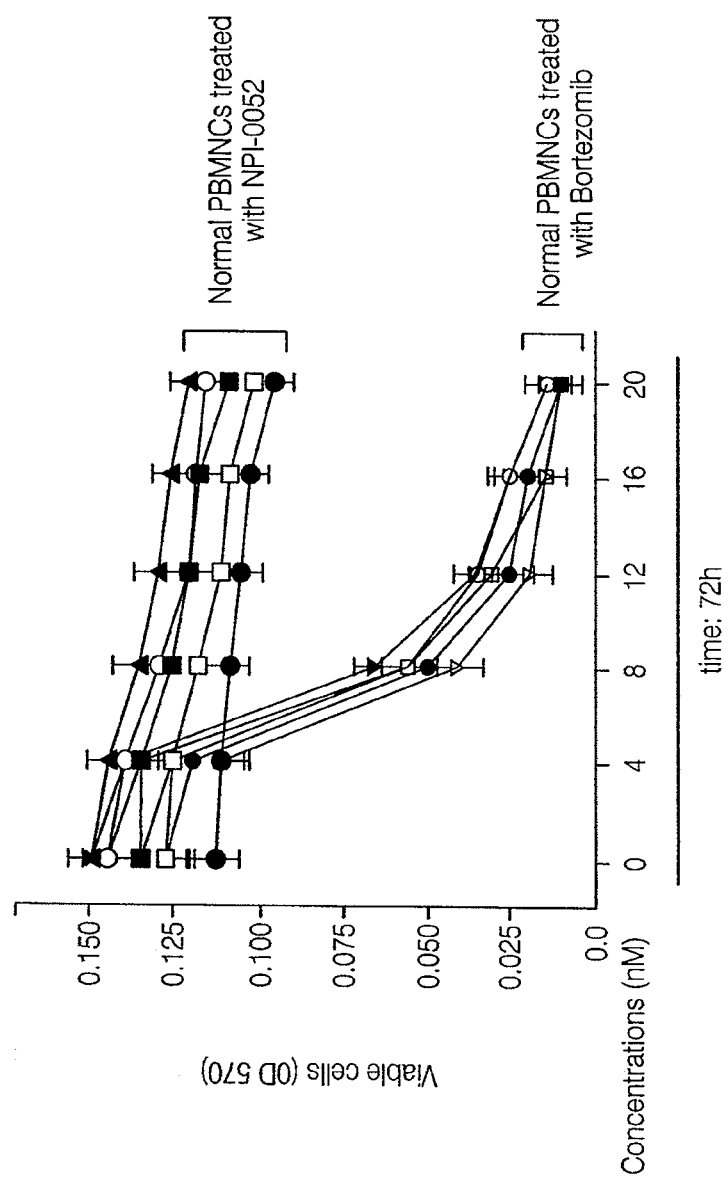
FIG. 13 illustrates viability of normal lymphocytes from five healthy donors treated with indicated concentrations of NPI-0052 or Bortezomib.

Bortezomib therapy is associated with toxicity in patients. Thus, the effects of the compound of formula (II) (X=Cl) and Bortezomib on normal cells was compared. Lymphocytes from five healthy donors were treated with various concentrations (0-20 nM) of the compound of formula (II) (X=Cl) or Bortezomib (0-20 nM) for 72 h and analyzed for cytotoxicity by an MTT assay. As seen in FIG. 13, the compound of formula (II) (X=Cl) does not significantly decrease the survival of normal lymphocytes (P=0.27 from J-T trend test), even at higher doses (20 nM). Results are the mean±SD of three independent experiments. In contrast, Bortezomib significantly decreases the viability of lymphocytes even at lower concentrations of 6-10 nM. Of note, $IC_{50}$ of patient MM cells is reached at concentrations of the compound of formula (II) (X=Cl) that have no effect on normal lymphocytes, whereas $IC_{50}$ of Bortezomib for MM cells triggers 50% decrease in viability of normal lymphocytes. Together, these data suggest that the compound of formula (II) (X=Cl) has selective anti-MM activity; and particularly, it is less toxic to normal cells than Bortezomib.

Whether the compound of formula (II) or Bortezomib alters proteasome activity in normal lymphocytes and skin fibroblasts was also examined. Both the compound of formula (II) (X=Cl) and Bortezomib significantly inhibited proteasome activity in these cells: 20 nM of the compound of formula (II) (X=Cl) or Bortezomib triggered 99% or 59±11% inhibition of Chymotrypsin-like proteasome activity, respectively (data not shown). Thus, although 20 nM of the compound of formula (II) (X=Cl) did not trigger significant cytotoxicity in normal lymphocytes, it reduced Chymotrypsin-like proteasome activity in these cells. Similarly, treatment of normal CCD-27sk fibroblasts at the IC50 for the compound of formula (II) (X=Cl) (317 nM) or Bortezomib (15 nM) also inhibited proteasome activity (data not shown).

Example 16

Figure 14A:
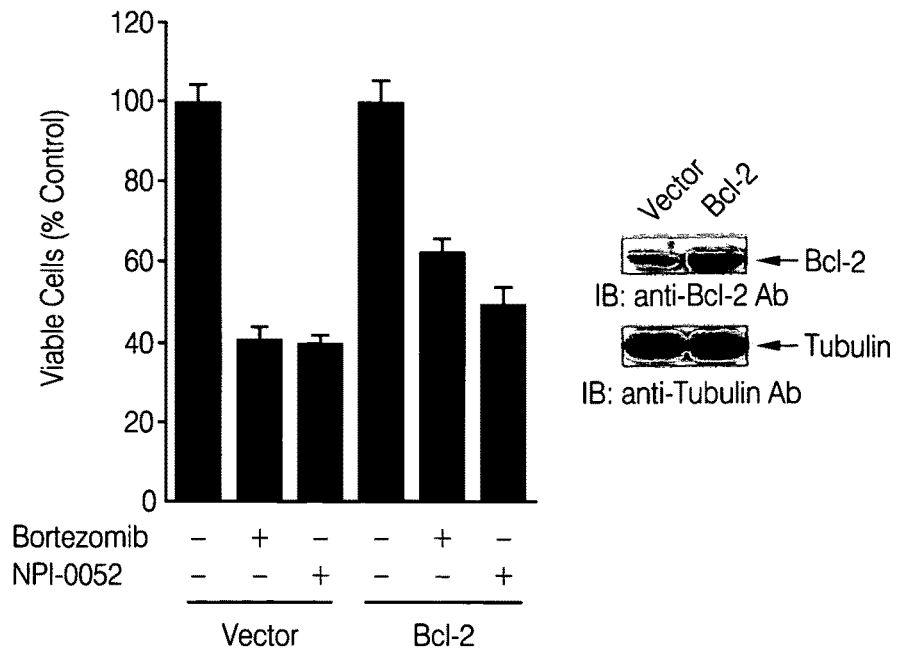
FIG. 14A illustrates MM.1S cell viability for cells transfected with vector alone or Bcl-2 after treatment with NPI-0052 or Bortezomib.
Figure 14B:
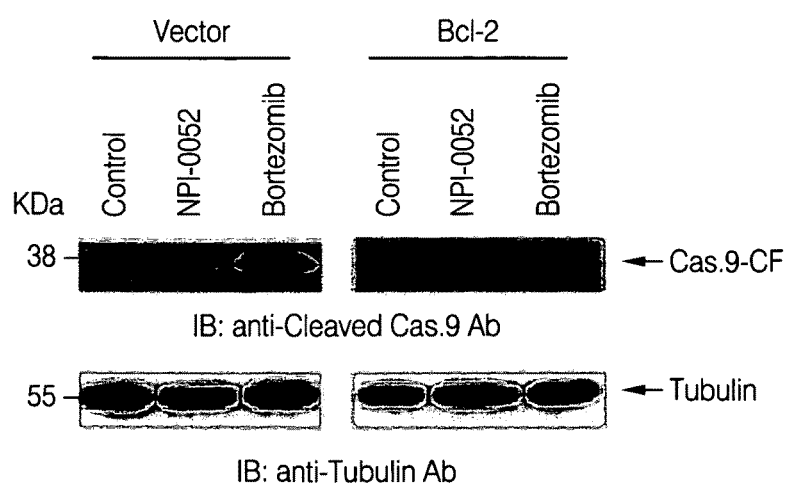
FIG. 14B depicts immunoblots of cytosolic extracts from vector- or Bcl-2-transfected MM.1S cells treated with NPI-0052 or Bortezomib.

Differential Effects on Bcl-2-Overexpressing MM Cells as Compared to Bortezomib During apoptosis Bax neutralizes the antiapoptotic function of Bcl-2, thereby facilitating the cyto-c release and caspase-9 activation. Bcl-2 also confers drug resistance in cancer cells, including MM, and provides partial protection against Bortezomib-induced killing. Therefore, whether ectopic expression of Bcl-2 in MM.1S cells affects the ability of the compound of formula (II) or Bortezomib to trigger cytotoxicity and postmitochondrial apoptotic signaling in MM cells was evaluated. Overexpression of Bcl-2 promoted a modest increase in viability of cells treated with both agents: for the compound of formula (II) (X=Cl), 50%±2.6% viability in Bcl-2-transfected cells versus 39%±1.5% viability in vector-transfected cells (p<0.05); and for Bortezomib, 61%±2.9% viability in Bcl-2-transfected cells versus 40%±2.1% viability in vector-transfected cells (p<0.05) (FIG. 14A). The increased survival of Bcl-2 transfectants in response to Bortezomib was greater (21%) than that in response to the compound of formula (II) (X=Cl) (11%) (p<0.04; n=3) (FIG. 14A). Moreover, Bortezomib triggered significant caspase-9 cleavage in control vector-transfected cells, which is markedly attenuated (3-fold decrease by densitometry) in Bcl-2-transfected cells; in contrast, compound of formula (II) (X=Cl)-induced caspase-9 cleavage is minimally affected by Bcl-2 overexpression (FIG. 14B). These findings, together with the viability results, suggest that Bcl-2 provides more protection against Bortezomib than the compound of formula (II).

Example 17

Combination Treatment

Figure 15:
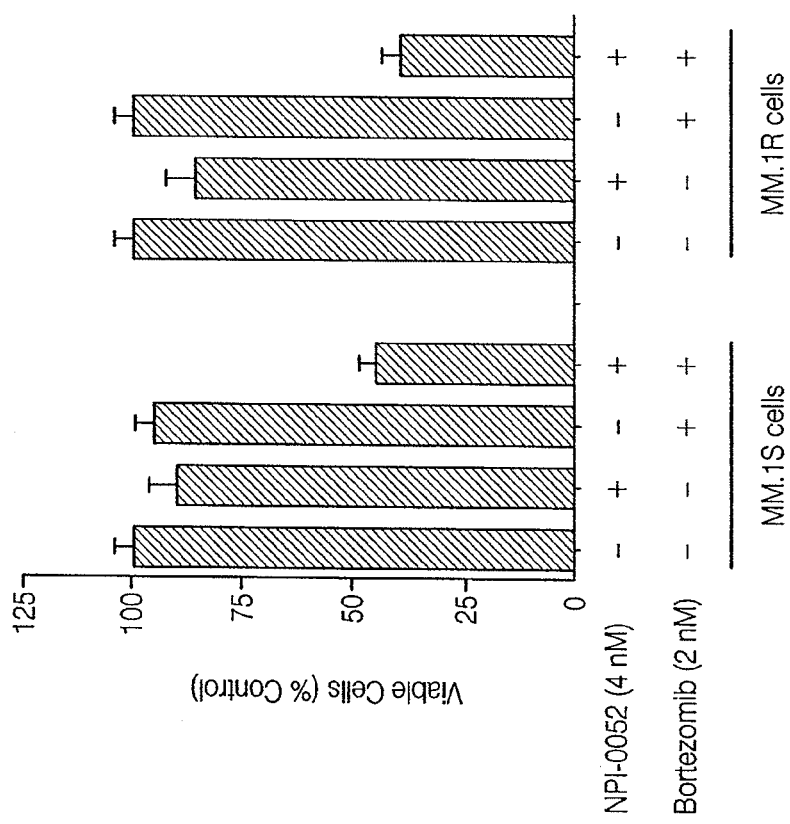
FIG. 15 illustrates cell viability of MM.1S and MM.1R MM cells treated with indicated concentration of NPI-0052, Bortezomib, or NPI-0052+Bortezomib.

As seen in FIG. 15, treatment of MM.1S or MM.1R MM cells with the compound of formula (II) (X=Cl) in combination with Bortezomib for 24 h induces synergistic growth inhibition. Results are mean±SD of three independent experiments (P<0.005). The interaction between anti-MM agents formula (II) (X=Cl) and Bortezomib was analyzed using isobologram analysis with "CalcuSyn" software program (Biosoft, Ferguson, Mo. and Cambridge, UK). Data from cell viability assay (MTT) were expressed as fraction of cells with growth affected (FA) in drug-treated versus untreated cells. The CalcuSyn program is based upon the Chou-Talalay method according to the following equation: "CI=(D)1/(Dx) 1+(D)2/(Dx)2+(D)1(D)2/(Dx)1(Dx)2", where (D)1 and (D)2 are the doses of drug 1 and drug 2 that have x effect when used in combination; and (Dx)1 and (Dx)2 are the doses of drug 1 and drug 2 that have the same x effect when used alone. When CI=1, this equation represents the conservation isobologram and indicates additive effects. CI values of <1.0 indicate synergism. A combination index (CI) of <1.0 was obtained for Bortezomib+NPI-0052, indicating synergism. Moreover, maximal anti-MM activity was observed when given concomitantly, rather than other treatment schedules. Low doses of combined compound of formula (II) (X=Cl) and Bortezomib does not significantly affect viability of normal PBMNCs (data not shown). Combination therapy with Bortezomib and the compound of formula (II) (X=Cl) therefore may: 1) allow use of sub-toxic concentrations of each agent; 2) delay or prevent development of drug-resistance; and 3) permit escalating synergistic doses of these agents to increase the apoptotic threshold.

What is claimed is:

1. A method of treating a neoplastic disease, comprising: administering to a patient inflicted with the neoplastic disease a compound of formula (I) or a pharmaceutically acceptable salt thereof:

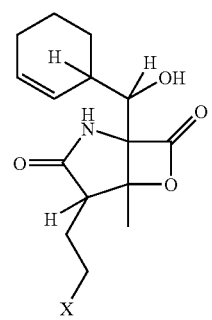

(I)

wherein X is selected from the group consisting of fluorine, chlorine, bromine or iodine, and wherein the neoplastic disease is resistant to a proteasome inhibitor.

2. The method of claim 1, wherein X is chlorine.

3. The method of claim 1, wherein the compound of formula (I) has the structure of formula (II):

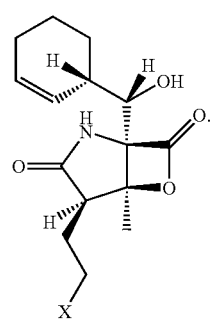

(II)

4. The method of claim 1, wherein the neoplastic disease is cancer.

5. The method of claim 4, wherein the cancer is selected from the group consisting of breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer.

6. The method of claim 5, wherein the cancer is selected from the group consisting of multiple myeloma, colorectal carcinoma, prostate carcinoma, breast adenocarcinoma, non-small cell lung carcinoma, and an ovarian carcinoma or melanoma.

7. The method of claim 6, wherein the cancer is a multiple myeloma.

8. The method of claim 1, wherein the patient is a human.

9. The method of claim 1, wherein the proteasome inhibitor is bortezomib.

* * * * *

UNITED STATES PATENT AND TRADEMARK OFFICE
CERTIFICATE OF CORRECTION

| | | |
|---|---|---|
| PATENT NO. | : 8,722,724 B2 | Page 1 of 1 |
| APPLICATION NO. | : 12/183007 | |
| DATED | : May 13, 2014 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 990 days.

Signed and Sealed this
Twenty-eighth Day of July, 2015

Michelle K. Lee
*Director of the United States Patent and Trademark Office*